US006146849A

United States Patent [19]
Pierce et al.

[11] Patent Number: 6,146,849
[45] Date of Patent: Nov. 14, 2000

[54] LECTINS AND CODING SEQUENCES

[75] Inventors: J. Michael Pierce; Kelley W. Moremen, both of Athens, Ga.; Jin Kyu Lee, San Francisco, Calif.

[73] Assignee: University of Georgia Research Foundation Inc., Athens, Ga.

[21] Appl. No.: 09/124,758

[22] Filed: Jun. 4, 1998

[51] Int. Cl.[7] .............................. C12N 1/21; C12N 5/10; C12N 15/12; C12N 15/63

[52] U.S. Cl. ..................... 435/69.1; 435/325; 435/252.3; 435/320.1; 536/23.1; 536/23.5

[58] Field of Search ................................. 536/23.1, 23.5; 435/325, 252.3, 320.1, 69.1

[56] References Cited

PUBLICATIONS

Bakos et al. (1990) "Enzymatic and Envelope–Converting Activities of Pars Recta Oviductal Fluid from *Xenopus laevis*" *Dev. Biol.* 138:169–176.

Bakos et al. (1990) "Physiochemical Characterization of Progressive Changes in the *Xenopus laevis* Egg Envelope following Oviductal Transport and Fertilization" *Biochemistry* 29:609–615.

Barondes, S.H. (1988) "Bifunctional Properties of Lectins: Lectins Redefined" *TIBS* 13:480–482.

Barondes and Roberson (1987) "*Xenopus laevis* Lectins" *Methods Enzymol.* 138:516–520.

Clark et al. (1987) "Toxin A from *Clostridium difficile* Binds to Rabbit Erythrocyte Glycolipids with Terminal Galα1–3Galβ1–4GlcNAc Sequences" *Arch. Biochem. Biophys.* 257:217–229.

Drickamer, K. (1995) "Increasing Diversity of Animal Lectin Structures" *Curr. Opin. Struct. Biol.* 5:612–616.

Drickamer and Taylor (1993) "Biology of Animal Lectins" *Annu. Rev. Cell Biol.* 9:237–264.

Genbank, Accession No. Z36760, Aug. 22, 1994.

Greve et al. (1985) "N–Acetyl–β–D–Glucosaminidase Activity in the Cortical Granules of *Xenopus laevis* Eggs" *Gamete Res.* 12:305–312.

Hsueh et al. (1986) "The Rat Liver Asialoglycoprotein Receptor Polypeptide Must Be Inserted into a Microsome to Achieve Its Active Conformation" *J. Biol. Chem.* 261:4940–4947.

Jia and Wang (1988) "Carbohydrate Binding Protein 35" *J. Biol. Chem.* 263:6009–6011.

Lee et al. (1997) Cloning and Expression of a *Xenopus laevis* Oocyte Lectin and Characterization of its mRNA Levels During Early Development *Glycobiology* 7(3):367–372.

Lee, J. K. (1997) "Discovery of a New Family of C–Type Vertebrate Lectins" *Dissertation submitted to the Graduate Faculty of The University of Georgia*.

Lindsay and Hedrick (1989) "Proteases Released from *Xenopus laevis* Eggs at Activation and Their Role in Envelope Conversion" *Dev. Biol.* 135:202–211.

Lindsay et al. (1988) "Egg Envelope Conversion following Fertilization in *Bufo japonicus*" *Dev. Biol.* 130:37–44.

Nishihara et al. (1986) "Isolation and Characterization of a Lectin from the Cortical Granules of *Xenopus laevis* Eggs" *Biochemistry* 25:6013–6020.

Nomura et al. (1995) "Occurrence of a Novel Fucose–Containing Pentaglycosylceramide With Blood–Group–B Active Determinant in Xenopus Blastula Cells: its Possible Involvement in Cell–Cell Adhesion" *Biochem. J.* 306:821–827.

Outenreath et al. (1988) "Endogenous Lectin Secretion into the Extracellular Matrix of Early Embryos of *Xenopus laevis*" *Dev. Biol.* 125:187–194.

Pepys and Baltz (1983) "Acute Phase Proteins with Special Reference to C–Reactive Protein and Related Proteins (Pentaxins) and Serum Amyloid A Protein" *Adv. Immunol.* 34:141–212.

Powell and Varki (1995) "I–type Lectins" *J. Biol. Chem.* 270:14243–14246.

Prody et al. (1985) "Purification and Characterization of an N–Acetyl–β–D–Glucosaminidase From Cortical Granules of *Xenopus laevis* Eggs" *J. Exp. Zool.* 235:335–340.

Quill and Hedrick (1996) "The Fertilization Layer Mediated Block to Polyspermy in *Xenopus laevis:* Isolation of the Cortical Granule Lectin Ligand" *Arch. Biochem. Biophys.* 333:326–332.

Roberson et al. (1985) "Galactoside–binding Serum Lectin of *Xenopus laevis*" *J. Biol. Chem.* 260:11027–11032.

Roberson and Barondes (1983) "*Xenopus laevis* Lectin Is Localized at Several Sites in Xenopus Oocytes, Eggs, and Embryos" *J. Cell Biol.* 97:1875–1881.

Roberson and Barondes (1982) "Lectin from Embryos and Oocytes of *Xenopus laevis*" *J. Biol. Chem.* 257:7520–7524.

Spiess and Lodish (1986) "An Internal Signal Sequence: The Asialoglycoprotein Receptor Membrane Anchor" *Cell* 44:177–185.

Strecker et al. (1995) "Primary Structure of 12 Neutral Oligosaccharide–Alditols Released from the Jelly Coats of the Anuran *Xenopus laevis* by Reductive β–Elimination" *Glycobiology* 5:137–146.

Tedder et al. (1989) "Isolation and Chromosomal Localization of cDNAs Encoding a Novel Human Lymphocyte Cell Surface Molecule, LAM–1" *J. Exp. Med.* 170:123–133.

(List continued on next page.)

*Primary Examiner*—Elizabeth Kemmerer
*Attorney, Agent, or Firm*—Greenlee Winner and Sullivan PC

[57] ABSTRACT

The present disclosure provides a novel family of C-type lectins from vertebrates. As specifically exemplified, this family of lectins includes a melibiose-specific lectin (XL35) from *Xenopus laevis* oocytes, and two human lectins, HL-3 and HL-13, specifically expressed in endothelial cells such as blood vessels, stomach, small intestine, heart and tissue and in small intestine, respectively. Amino acid sequences of the lectin proteins are provided herein, together with the nucleotide sequences encoding these proteins.

23 Claims, 8 Drawing Sheets

OTHER PUBLICATIONS

Walsh et al. (1996) "Fine Mapping of the Human Pentraxin Gene Region on Chromosome 1q23" *Immunogenetics* 44:62–69.

Watson et al. (1990) "Genomic Organization of the Selectin Family of Leukocyte Adhesion Molecules on Human and Mouse Chromosome 1" *J. Exp. Med.* 172:263–272.

Wyrick et al. (1974) "Agglutination of Jelly Coat and Cortical Granule Components and the Block to Polyspermy in the Amphibian *Xenopus laevis*" *Proc. Natl. Acad. Sci. USA* 71:2067–2071.

Zalik, S.E. (1991) "On the Possible Role of Endogenous Lectins in Early Animal Development" *Anatomy and Embryology* 183:521–536.

```
                     #
HL-3     1   ......MNQLSFLLFLIATTRGWSTDEANT...YFKEWTCS..SSPSLP
HL-13    1   MLSMLRTMTRLCFLLFFSVATSGCSAAAASSLEMLSREFETCAFSFSSLP
XL35     1   ......MLVHILLLLVTGGLSQSCDPVVIVASKNMVKQLDCDKF......
             #                        #
HL-3    39   RSCKEIKDECPSAFDGLYFLRTENGVIYQTFCDMTSGGGGWTLVASVHEN
HL-13   51   RSCKEIKERCHSAGDGLYFLRTKNGVVYQTFCDMTSGGGGWTLVASVHEN
XL35    39   RNCKEIKDSNEEAQDGIYTLTSPDGISYQTFCDMTTNGGGWTLVASVHEN
             #
HL-3    89   DMRGKCTVGDRWSSQQGSKADYPEGDGNWANYNTFGSAEAATSDDYKNPG
HL-13  101   DMRGKCTVGDRWSSQQGNKADYPEGDGNWANYNTFGSAEAATSDDYKNPG
XL35    89   NMAGKCTIGDRWSSQQGNRADYPEGDGNWANYNTFGSAGGATSDDYKNPG
                                      *        *
HL-3   139   YYDIQAKDLGIWHVPNKSPMQHWRNSSLLRYRTDTGFLQTLGHNLFGIYQ
HL-13  151   YYDIQAKDLGIWHVPNKSPMQHWRNSALLRYRTNTGFLQRLGHNLFGIYQ
XL35   139   YYDIEAYNLGVWHVPNKTPLSVWRNSSLQRYRTTDGILFKHGGNLFSLYR
                   #                  *     *
HL-3   189   KYPVKYGEGKCWTDNGPVIPVVYDFGDAQKTASYYSPYGQREFTAGFVQF
HL-13  201   KYPVKYRSGKCWNDNGPAIPVVYDFGDAKKTASYYSPYGQREFVAGFVQF
XL35   189   IYPVKYGIGSCSKDSGPTVPVVYDLGSANLTASFYSPGFRSQFTPGYTQF
                         #          #     # *              #
HL-3   239   RVFNNERAANALCAGMRVTGCNTEHHCIGGGGYFPEASPQQCGDFSGFDW
HL-13  251   RVFNNERAANALCAGIKVTGCNTEHHCIGGGGFFPQGKPRQCGDFSAFDW
XL35   239   RPINTEKAALALCPGMKMESCNVEHVCIGGGGYFPEADPRQCGDFAAYDF

HL-3   289   SGYGTHVGYSSSREITEAAVLLFYR
HL-13  301   DGYGTHVKSSCSREITEAAVLLFYR
XL35   289   NGYGTKKFNSAGIEITEAAVLLFYL
```

LECTINS AND CODING SEQUENCES

CROSS REFERENCE TO RELATED APPLICATIONS

The present application claims priority from United States Provisional Patent Application No. 60/048,507, filed Jun. 4, 1997.

ACKNOWLEDGEMENT OF FEDERAL RESEARCH SUPPORT

This invention was made, at least in part, with funding from the National Institutes of Health. Accordingly, the United States Government has certain rights in this invention.

BACKGROUND OF THE INVENTION

The field of the present invention is the area of lectins, especially those derived from animals, and nucleotide sequences encoding same.

Recently, Barondes redefined the lectins as proteins, other than enzymes and antibodies, that have one or more binding sites for specific carbohydrate sequences, and that may also display additional domains capable of interacting with molecules other than carbohydrates in nature [Barondes, S. H. (1988) TIBS 13, 480–482]. While most lectins have the ability to agglutinate specific types of cells, not all lectins are necessarily agglutinins.

Lectins were first described in plants in relation to their cell agglutinating properties [Goldstein and Hayes (1978) Adv. Carbohydrate Chem. Biochem. 35, 127–340; Sharon and Lis (1989) Science 246, 227–234]; these molecules have been discovered in microorganisms, plants, and animal tissues [Barondes, S. H. (1986) Vertebrate Lectins: Properties and Functions. The Lectins: Properties, Functions and Applications in Biology and Medicine. (Liener, I. E., Sharon, N., and Goldstein, I. J., Eds.), New York; Gabius et al. (1986) Cancer Res. 6, 573–578; Lotan and Raz (1988) J. Cell Biochem. 37, 107–117; Lotan et al. (1990) in Proc. 12th Internat. Lectin Conf., pp. 14, Davis, USA; Zalik and Milos (1986) Endogenous lectins and cell adhesion in embryonic cells. Developmental Biology, a Comprehensive Synthesis. (Browder, L. W., Ed.), 11, Plenum Press, New York]. It has been shown that lectins mediate certain biological recognition events in plants and in animal tissues of embryonic and adult origins, in tumor cell lines, and in microbial adhesion.

Lectins are diverse in structure and are characterized by their ability to bind carbohydrates with considerable specificity. In spite of the vast diversity among lectins, however, two aspects of their organization are generally conserved. First, the sugar-binding activity can be ascribed to a limited portion of most lectin molecules, typically a globular carbohydrate-recognition domain (CRD) of less than 200 amino acids [Drikamer, K. (1993) Curr. Opin. Structural Biol. 3, 393–400]. Second, comparison of CRDs reveals that many are related in amino acid sequence.

Animal lectins have been found associated with the cell surface, the cytoplasm, and the nucleus [Barondes, 1986, supra; Jia and Wang (1988) J. Biol. Chem. 263, 6009–6011]. At the cell surface, lectins can act as receptors involved in selective intercellular adhesion and cell migration [Lehmannet al. (1990) Proc. Natl. Acad. Sci. USA 87, 6455–6459; Regan et al. (1986) Proc. Natl. Acad. Sci. USA 83, 2248–2252; Rosen, S. D. (1989) Curr. Opinion Cell Biol. 1, 913–919] as well as in the recognition of circulating glycoproteins [Ashwell and Harford (1982) Ann. Rev. Biochem. 51, 531–554; Laing et al. (1989) J. Biol. Chem. 264, 1907–1910]. Lectins have also been shown to function as receptors for the extracellular matrix proteins, elastin and laminin [Cooper et al. (1990) J. Cell Biol. 111, 13a; Hinek et al. (1988) Science 239, 1539–1541; Mecham et al. (1989) J. Biol. Chem. 264, 16652–16657; Woo et al. (1990) J. Biol. Chem. 265, 7097–7099; Zhou and Cummings (1990) Arch. Biochem. Biophys. 281, 27–35] and for glycosaminoglycans that presumably mediate the binding of the proteoglycan to the sugars of other matrix glycoproteins [Doege et al. (1987) J. Biol. Chem. 262, 17757–17767; Gallager, J. T. (1989) Curr. Opinion Cell Biol. 1, 1201–1218; Hallberg et al. (1988) J. Biol. Chem. 263, 9485–9490; Krusius et al. (1987) J. Biol. Chem. 262, 13120–13125]. Taken together, these results reflect a fundamental role for lectins in the mediation of cell interactions, and in the organization of the extracellular matrix.

Animal lectins can be classified into distinct families based on protein sequence homologies [Drickamer and Taylor (1993) Annu. Rev. Cell Biol. 9, 237–264; Powell, L. D., and Varki, A. (1995) J. Biol. Chem. 270, 14243–6]. Most fall into one of five major groups: C-type or Ca2+-dependent lectins, Gal-binding galectins, P-type Man 6-phosphate receptors, I-type lectins including sialoadhesins and other immunoglobulin-like sugar-binding lectins, and L-type lectins related in sequence to the leguminous plant lectins [Drickamer, K. (1995) Curr. Opin. Struct. Biol. 5, 612–6]. In addition, all of the structurally characterized bacterial toxins and adhesins that use carbohydrates as cellular receptors display common structural features [Burnette, W. N. (1994) Structure 2, 151–158].

The C-type CRDs form the most diverse class of animal lectins. The various groups of C-type animal lectins are found in serum, the extracellular matrix, and in membranes, and they function as endocytic receptors, adhesion molecules, and in humoral defense. C-type lectins share the property of binding their ligands in a calcium ion-dependent manner, but they fall into a number of distinct groups, in which the C-type CRD is combined with other protein segments. Sequence alignments have led to the identification of more than 50 proteins that contain domains related to these CRDs. Comparison of these sequences reveals the presence of a common sequence motif consisting of 14 invariant and 18 highly conserved residues (FIG. 2) [Drickamer, 1993, supra]. However, there are C-type (calcium-dependent) lectins which do not have a characteristic CRD.

The mammalian asialoglycoprotein receptors (ASGPRs) are heterooligomeric receptors that are abundantly expressed on the basolateral surface of the hepatic plasma membrane [Lodish, H. F. (1991) Trends Biochem. Sci. 16, 374–377]. ASGPRs functions as endocytic receptors that rapidly bind and internalize galactose-terminated glycoproteins (asialoglycoproteins, ASGP) from the circulation [Lodish, 1991, supra; Spiess, M. (1990) Biochemistry 29, 10009–10018]. The ASGPR in the mouse is composed of two highly homologous subunits, murine hepatic lectin (MHL) 1 and 2, each consisting of a cytosolic $NH_2$-terminal domain, a single transmembrane segment [Spiess, M. (1986) Cell 44, 177–185], a stalk domain, and a $Ca^{2+}$-dependent carbohydrate binding domain at the COOH terminus [Hsueh et al. (1986) J. Biol. Chem. 261, 4940–4947].

Under normal conditions, the penultimate galactose residues of glycoproteins are masked by terminal sialic acid moieties. Upon enzymatic removal of sialic acid, the newly terminal galactose residues constitute the recognition determinants for ASGPR [Ashwell, 1982, supra; Schwartz, A. L.

(1984) *CRC Crit. Rev. Biochem.* 51, 531–554]. Binding of ligands to ASGPR depends on (i) the amount and positioning of terminal galactose residues on the ligands [Lee et al. (1983) *J. Biol. Chem.* 258, 199–202; Hardy et al. (1985) *Biochemistry* 24, 22–28; Chiu et al. (1994) *J. Biol. Chem.* 269, 16195–16202]; (ii) the presence of Ca2+ in an optimal concentration of 0.1–2 mM [Weigel, P. H. (1980) *J. Biol. Chem.* 255, 6111–6120]; and (iii) a pH above 6.5 [Schwartz and Rup (1983) *J. Biol. Chem.* 258, 11249–11255].

Using cross-linking experiments on the purified rat receptor and hepatocyte membranes, Halberg et al. concluded that the major and minor receptor species form independent homooligomers in the membrane [Halberg et al. (1987) *J. Biol. Chem.* 262, 9828–9838]. It has been shown that the individual ASGPR subunits have to interact with one another to form a single multicomponent receptor [McPhaul, M. and Berg, P. (1986) *Proc. Natl. Acad. Sci. USA* 83, 8863–8867; Sawer et al. (1988) *J. Biol. Chem.* 263, 10534–10538; Bischoff et al. (1988) *J. Cell. Biol.* 106, 1067–1074; Shia and Lodish (1989) *Proc. Natl. Acad. Sci. USA* 86, 1158–1162; Rice et al. (1990) *J. Biol. Chem.* 265, 18429–18434; Henis et al. (1990) *J. Cell Biol.* 111, 1409–1418; Graeve et al. (1990) *J. Biol. Chem.* 265, 1216–1224].

Recently, amino acid residues likely to be involved in the selective binding of GalNAc to MHL-1 (murine hepatic lectin-1) have been identified by analysis of chimeric and mutagenized versions of the CRDs [Iobst and Drickamer (1996) *J. Biol. Chem.* 271, 6686–6693]. In addition, Braun et al. observed that ASGPR-deficient mice did not result in an increase in the absolute serum concentration of endogenous galactose-terminated glycoproteins. In vitro competition experiments, however, suggested that other ligands for ASGPR accumulate in their circulation. The nature of the alternative ASGPR ligands is currently unknown [Braun et al. (1996) *J. Biol. Chem.* 271, 21160–21166].

SUMMARY OF THE INVENTION

The present invention provides lectins derived from animal cells and nucleotide sequences encoding same, where these lectins are members of a novel gene family of calcium-dependent lectins. One specifically exemplified member of this new lectin family is the soluble, calcium-dependent lectin from *Xenopus laevis* termed XL35 herein; it has binding specificity for melibiose, an amino acid sequence as given in SEQ ID NO:2, and a specifically exemplified coding sequence as given in SEQ ID NO:1, nucleotides 33 to 974. A second specifically exemplified member of this calcium dependent lectin family is from human; it is termed HL-3 herein, and is identified by the amino acid sequence of SEQ ID NO:4, it is expressed in a characteristic subset of endothelial tissue including heart, colon, small intestine, thymus, ovary, testis, spleen, skeletal muscle, placenta and spleen. The coding sequence is SEQ ID NO:3, nucleotides 107 to 1048. A third specifically exemplified member of this family is human HL-13; it has an amino acid sequence as given in SEQ ID NO:6, and a coding sequence as given in SEQ ID NO:5, nucleotides 34 to 1011. HL-13 is specifically expressed in small intestine.

It will be understood in the art that other C-type lectins and coding sequences for same can be isolated and identified by nucleotide sequence homology, for example, as determined in hybridization experiments using conditions of moderate stringency (See, e.g., Hames and Higgins (1985) *Nucleic Acid Hybridization*, IRL Press, Washington, D.C.) employing the mature XL35, mature HL-3 or mature HL-13 polypeptide coding sequence information provided herein. A preferred probe is a nucleic acid molecule having a sequence as given in SEQ ID NO:1, nucleotides 118–518; SEQ ID NO:3, nucleotides 305–554, SEQ ID NO:5, nucleotides 268–517, or a sequence complementary to one of the foregoing.

Lectin genes having at least about 70% nucleotide sequence identity to the exemplified mature XL35 protein coding sequence can be readily isolated employing well-known hybridization assays, polymerase chain reaction methods or screens. Exemplary hybridization conditions of moderate stringency are those in which hybridization and/or washing is carried out at 50 to 65° C., 1×SSC, 0.1% SDS. These conditions allow hybridization of sequences having at least about 80 to 95% nucleotide sequence identity. Conditions of high stringency are those where hybridization and washing are carried out at 65 to 68° C., 0.1×SSC and 0.1% SDS. Highly stringent hybridization conditions allow hybridization of nucleic acid molecules having about 95 to 100% sequence identity. Conditions of low stringency are those where hybridization and washes are carried out at 40 to 50° C., 6×SSC and 0.1% SDS. These conditions allow one to detect specific hybridization of nucleic acid molecules having at least about 50 to 80% nucleotide sequence identity. Such procedures are particularly useful for the isolation of such lectins from amphibians and from other animals, including animals, in particular humans. Functional equivalents of the lectins of the present invention, as exemplified by XL35, HL-3 and HL-13 are proteins having the biological activity of calcium dependent lectins XL35 and/or HL-3 or HL-13 and which are substantially similar in structure, i.e., amino acid sequence, to the exemplified lectins as given in SEQ ID NO:2, SEQ ID NO:4 and SEQ ID NO:6, respectively. Other members of the C-type lectin group of the present invention can be readily isolated without the expense of undue experimentation using antibody preparations having specificity to XL35, HL-3 or HL-13 in screens of expression clone libraries. In sequence comparisons, gaps introduced to improve alignment are treated as mismatches.

Mature calcium-dependent lectins substantially similar to XL35, HL-3 and HL-13 mature proteins include those which are at least about 60 to 80% identical in amino acid sequence to XL35, HL-3 or HL-13. Substantially similar lectins also include those which have at least about 80% amino acid sequence similarity to XL35, HL-3 or HL-13, which allows conservative amino acid substitutions for the amino acids of XL35 and HL-3 or HL-13. In sequence comparisons, gaps introduced to optimize alignment to a target sequence are treated as a mismatch to the target (reference) sequence. This lectin family lacks the CRD characteristic of many Ca-dependent lectins (See FIGS. 1 and 2). It is appreciated by those in the art that protein function may be unaffected by minor structural modifications, particularly if those structural modifications are substitutions of amino acids which are similar in chemical and physical properties. Structural modification, including amino acid deletions and insertions, may be tolerated without effect on functionality.

Genes encoding calcium-dependent lectins which are functionally equivalent to XL35 and/or HL-3 and/or HL-13 can be isolated and identified or otherwise prepared by any means known to the art, especially by reliance on sequence information provided herein. For example, amino acid sequence homology and/or nucleotide sequence homology as measured by hybridization methods can be coupled with methods described herein for assessing carbohydrate binding to isolate functional animal-derived lectins. PCR methods, for example, combined with other art-known techniques and the teachings herein can be employed to isolate genes encoding lectins that are functionally equivalent to those of the present invention. The information provided herein coupled with known methodology regarding protein and DNA synthesis, conservation of properties between amino acids and codon usage allows those of ordinary skill in the art to readily design and synthesize lectins and lectin genes which are functional equivalents of XL35, HL-3 OR HL-13.

BRIEF DESCRIPTION OF THE DRAWINGS

FIG. 2 is a comparison of deduced amino acid sequences of HL-3, HL-13 and XL35. See also SEQ ID NOs: 4, 6 and 2, respectively. Amino acid residues of HL-3, HL-13 and XL35 are shown. Identical amino acid residues are black boxed, those in similar amino acid residues are gray boxed. The putative signal peptide sequences are underlined: Asterisks (*), possible N-glycosylation sites. #, conserved cysteine residues.

DETAILED DESCRIPTION OF THE INVENTION

Figure 1:
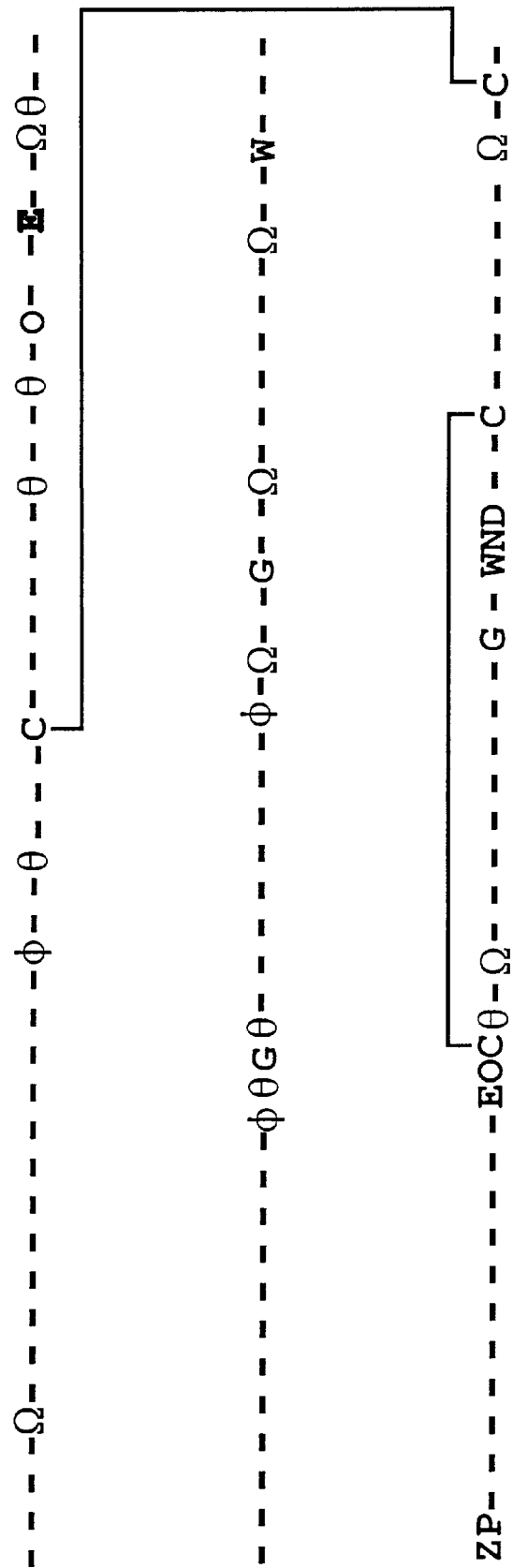
FIG. 1 illustrates the sequence motif of C-type CRDs [see also Drickamer, 1993]. Invariant residues are indicated as one letter amino acid abbreviations. Residues that are conserved in character are designated: phi, aromatic; theta, aliphatic; omega, either aromatic or aliphatic; and O, oxygen-containing.

Xenopus laevis oocytes and embryos contain soluble, calcium-dependent, lectins which form multimers of about 500 kDa [Nishihara et al. (1986) Biochemistry 25, 6013–20; Roberson and Barondes (1982) J. Biol. Chem. 257, 7520–7526]. On reducing SDS-PAGE gels these lectins migrate as overlapping diffuse bands of about 45 and 43 kDa [Outenreath et al. (1988) Dev. Biol. 125, 187–94; Roberson and Barondes, 1982, supra. These proteins are contained within the cortical granules of the oocytes, and they are released from the cortical granules at fertilization [Nishihara, 1986, supra; Wyrick et al. (1974) Proc. Natl. Acad. Sci. USA 71, 2067–71]. The lectin accounts for 77% of the contents of the cortical granules, where it is associated with trypsin and chymotrypsin-like proteases [Lindsay and Hedrick (1989) Dev. Biol. 135, 202–211], and glycosidases [Greve et al. (1985) Gamete Res. 12, 305–312; Prody et al. (1985) J. Exp. Zool. 235, 335–340]. Release of the lectin is believed to contribute to the transformation of the fertilization envelope that blocks sperm penetration and subsequent polyspermy [Zalik, S. E. (1991) Anatomy and Embryology 183, 521–536]. The block to polyspermy consists of a fast, transient membrane depolarization which is replaced by a slower, permanent alteration of the surrounding extracellular matrix (vitellin envelope (VE) and jelly). In the presence of the cortical granule exudate, the VE undergoes a conformational change known as "hardening" (an increased resistance to physical deformation, thermal dissolution, and proteolysis), alterations in chemical reactivities, and a limited proteolysis of two related glycoproteins indirectly caused by an oocyte protease [Bakos et al. (1990) Dev. Biol. 138, 169–176; Bakos et al. (1990) Biochemistry 29, 609–615; Lindsay et al. (1988) Dev. Biol. 130, 37–44; Lindsay and Hedrick (1989) Dev. Biol. 135, 202–211].

Proteins purified from frog oocytes by melibiose affinity chromatography agglutinate trypsinized rabbit erythrocytes in the presence of Ca++, and this reaction is strongly inhibited by α-galactosides such as melibiose, suggesting that the lectins bind to the abundant glycolipids on these erythrocytes terminated by α-galactose residues [Clark et al. (1987) Arch. Biochem. Biophys. 257, 217–219].

Recently, Quill et al. developed a quantitative assay for the cortical granule lectin (CGL) ligand in the Xenopus laevis egg extracellular matrix. Using this assay, the CGL ligand was purified by gel filtration, anion-exchange, and CGL affinity chromatography [Quill and Hedrick (1996) Arch. Biochem. Biophys. 333, 326–332]. The purified ligand was a single heavily glycosylated, high-molecular weight component (Mr>250,000). The CGL ligand was rich in the potentially glycosylated β-hydroxy amino acids, Ser, Thr, and Gly, which are typical of glycoproteins containing O-linked glycans (such as mucins). The treatment of the CGL ligand with N-glycanase did not affect the binding of CGL. These authors have observed that ligand function is lost under hydrolysis conditions which cleave O-linked glycans (alkaline β-elimination). Digestion of the ligand with several exoglycosidases showed that α-galactoside residues are an essential carbohydrate moiety recognized by CGL. The structure of several neutral oligosaccharides released from glycoprotein of *Xenopus laevis* jelly by β-elimination has been reported [Strecker et al. (1995) *Glycobiology* 5, 137–46, 1995]. Three of these oligosaccharide structures were found to contain a terminal α1,4-linked galactose residue.

Nomura et al. demonstrated that novel neutral glycosphingolipids (XN-1 and XN-2) recognized by anti-blood-group-B (Galα1,3(Fucα1,2)Galβ1,4/3GlcNAcβ1-R) antibody exist in extracts of unfertilized *Xenopus laevis* eggs [Nomura et al. (1995) *Biochem. J*. 306, 821–7]. Both XN-1 and XN-2 had an identical pentaoligosaccharide structure, but differed in their ceramide moieties. The structure of their oligosaccharides is Galα1,3(Fucα1,2)Galβ1,3Galβ1,4-Glcβ1,1'Cer. Immunohistochemical studies using monoclonal antibody against blood-group B oligosaccharide showed that B antigens exist on the blastomere cell surface [Nomura, 1995, supra]. $Ca^{2+}$-dependent cell-cell adhesion of blastomeres was also inhibited by the addition of purified B type antigen, including protease-digested B-reactive glycopeptide. These glycolipids or glycoproteins that have terminal α-galactose are candidates for the XL35 ligand.

After fertilization, lectins with very similar physical properties and ligand specificities to the oocyte melibiose-binding lectin have been purified from blastulae [Roberson, 1982, supra]. Moreover, a polyclonal antibody prepared against the oocyte lectin preparation showed binding to cleavage furrows and to areas of active cell migration [Roberson and Barondes (1983) *J. Cell Biol*. 97, 1875–1881], including the blastopore region and the roof of the blastocoel [Outenreath, 1988, supra]. It has been suggested that the lectins are involved in cell adhesion and migration at these locations. In order to define in detail the structure and function of the lectins during fertilization and early development, we have affinity-purified the oocyte lectin on immobilized melibiose [Roberson, 1982, supra; Roberson et al. (1985) *J. Biol. Chem*. 260, 11027–32].

We have isolated and characterized cDNA clones encoding the *Xenopus laevis* oocyte, calcium-dependent lectin, termed XL35 herein. After obtaining internal peptide sequences from the purified oocyte lectin, a PCR-based cloning approach allowed the isolation of full length cDNAs from an ovary λgt11 library. These CDNAs encode a protein of 313 amino acids with three potential N-linked oligosaccharide sites. The XL35 deduced amino acid sequence is given in SEQ ID NO:2; potentially glycosylated Asn residues are at positions 154, 163 and 217 in FIG. 2. Although this lectin requires calcium ions for oligosaccharide binding, its sequence does not contain the sequence motif characteristic of most C-type lectins. Southern blot analysis revealed a single hybridizing band in *Xenopus laevis*, arguing against the existence of a multi-gene family in frog.

Table 1 provides the nucleotide and amino acid sequences of XL35. The position in the *Xenopus laevis* lectin coding region that was used as a hybridization probe in Southern and Northern blots is indicated by an underline. The positions in the coding region corresponding to the initial primers designed from empirically determined peptide sequences are denoted by dotted underlines. Asterisks below the peptide sequence indicate potential N-glycosylation sites.

To examine the expression patterns of lectin mRNA at fertilization and during embryo development, Northern analysis was performed on total RNA purified from Stage VI oocytes and from embryos at various stages of development. Northern analysis shows that relatively high levels of XL35 mRNA were present in the Stage VI oocytes and persisted through gastrulation, and then declined. Compared to the levels of expression in gastrulae, very little XL35 mRNA was present in hatching tadpoles. The same blot was then probed with a cDNA encoding a fragment of mitochondrial rRNA in order to normalize these results to the amount of RNA in each lane of the blot. Since it is highly unlikely that maternal mRNAs persist until tadpole stages, and because there is an increase in RNA levels at gastrulation, we conclude that XL35 mRNA is newly transcribed at the mid-blastula transition, along with many other zygotic RNAs. The fact that these RNAs are transcribed zygotically, as well as maternally, strongly supports the hypothesis that XL35 displays multiple functions during fertilization and development, consistent with the results of immunolocalization experiments.

The *Xenopus laevis* oocyte lectin purified by affinity chromatography on melibiose-Sepharose [Roberson, 1982, supra], exhibits diffuse bands at about 45 and 43 kDa after SDS-PAGE. Exhaustive treatment of the purified preparation with N-glycanase, which cleaves Asn-linked oligosaccharides, and subsequent SDS-PAGE, revealed a single major band at about 35 kDa. These results demonstrate that the oocyte lectin, termed XL35, is expressed as a single polypeptide and that the diffuse protein bands observed after affinity purification differ primarily in their N-linked oligosaccharide structures.

SDS-PAGE and Western blot analyses under non-reducing conditions showed several high molecular weight bands (>300 kDa) indicating the presence of multimeric forms of XL-35. These results suggest that multimerization of XL35 is mediated by interchain disulfide bonds. Large differences in the apparent molecular size of XL35 have been observed using HPLC size fractionation under reducing versus non-reducing conditions. Treatment of multimeric XL35 with 10 mM DTT allows the recovery of biologically active XL35 monomers which bind to oligosaccharides in the oocyte jelly coat.

To demonstrate that the XL35 cDNA indeed encodes the oocyte lectin purified by melibiose chromatography, the full length of XL35 cDNA was expressed in *E. coli*. The lectin was then purified, renatured, and assayed for activity.

The sequence encoding XL35 was modified by PCR to introduce a SalI restriction site at the predicted signal sequence cleavage site (Table 1) and cloned into the pQE-9 QIAexpress vector such that when expressed in *E. coli*, the resulting recombinant protein contained 6 histidine residues at its N-terminus. *E. coli* cells transformed with this construct were induced with IPTG to express the lectin, a protein with apparent molecular mass of 35 kDa. After harvesting, the cells were disrupted in guanidinium hydrochloride, and the extract was chromatographed on a $Ni^{++}$-NTA column that strongly binds to the $(His)_6$ residues engineered at N-terminal end of XL35. The apparent molecular weight of the recombinant protein bound by this column was about 35 kDa. After exchanging the guanidinium HCl buffer for one with 8 M urea, elution of the recombinant lectin from the affinity column was accomplished by lowering the pH to 4.5. The eluted fractions contained a single major band at 35 kDa, and analysis of the N-terminal sequence demonstrated it to be XL35. The purified recombinant lectin was assayed for its ability to agglutinate trypsinized, fixed rabbit erythrocytes. When all the urea was removed (by dialysis) from the solution containing the recombinant lectin, the lectin slowly precipitated, perhaps due to its lack of glycosylation. In 2 M urea, however, the recombinant lectin agglutinated trypsinized and fixed rabbit erythrocytes, and the agglutination was similar to the activity observed with the affinity-purified oocyte lectin. Moreover, the recombinant XL35 agglutination activity was completely inhibited by 0.1 M EDTA and by 0.25 M melibiose, but not by 0.25 M sucrose. These characteristics are similar to those observed for the affinity-purified oocyte lectin [Roberson, 1982, supra]. The melibiose affinity-purified oocyte lectin was also active in 2 M urea with the same specificity of binding, but with significantly lower specific activity than when analyzed without urea. Thus, the recombinant, non-glycosylated lectin encoded by the XL35 cDNA corresponds to the oocyte lectin purified by melibiose chromatography.

The Xenopus XL-35 cDNA sequence was analyzed using FASTA and TBLST programs to search for DNA sequence similarity. A single entry identified as significantly homologous was a 251 bp cDNA sequence from a human heart cDNA library (GenBank accession number Z36760) as an EST (expressed sequence tag) (Tables 2A–2B). Using the human EST sequence to design oligonucleotide primers, an amplimer was obtained from human liver, spleen, and placenta cDNA sources that was essentially identical (>98%) in sequence to the human heart cDNA sequence in the database. This amplimer was used to probe Northern blots of various human tissue RNAs and strong signals were detected from a ~1.3 kb mRNA in heart and small intestine.

Tables 2A–2B illustrate the results of TBLAST search with XL35 cDNA sequences. In the process of cloning XL35, the derived DNA sequence was used to search for DNA sequence and protein sequence similarity. The human heart-expressed sequence tag (EST), 251 bp, was found in GenBank sequence database using TFASTA and TBLAST searches (Table 2A). This sequence (Genbank, Z36760) showed 74% identity at DNA sequence level and 83% identity at amino acid level with that of XL35. The subject sequence indicates the deduced amino acid sequence from human heart EST sequence. Table 2B represents the DNA sequence of the heart EST sequence. The primers (underlined sequence) were designed for PCR reaction with human placenta, liver, and thymus cDNA as templates and the amplimer was used for cDNA screening of human homologs of XL35.

Figure 3A:
FIG. 3 compares hydropathy plots of XL35, HL-3 and HL-13. Each was obtained from deduced amino acid sequences using the pepplot program of the University of Wisconsin Genetics Computer Group (GCG software). The hydrophobicities were calculated by Hopp-Woods' (dotted line) and Kyte-Dolittle's (solid line) method. Each N-terminal end of XL35, HL-3 and HL-13 has hydrophobic amino acid residues indicating a signal peptide sequence. None of the three lectins has a predicted transmembrane domain.
Figure 3B:
Figure 3C:

The amplimer was used to probe a human small intestine λgt 10 cDNA library, and a total of 13 positive plaques showing different sizes between 0.7 and 2.4 kb were isolated. DNA sequences were determined for 7 cDNA clones that had a size greater than 1.0 kb. Sequence data indicated that six clones are identical (named HL-13), but only one clone (named HL-3) showed a different sequence (Tables 4–5 and FIG. 2). These two cDNA sequences showed 85% identity to one another at the deduced amino acid level (FIG. 2). A striking result was obtained when the deduced amino acid sequence of the two human homologs was aligned with that of XL-35. The amino acid identity between HL-3 and XL-35 was 60% (similarity, 74%) with a 56% amino acid identity (similarity, 74%) between HL-13 and XL35. HL-3 is the same size as XL35, 313 amino acids, while HL-13 has 325 amino acids. HL-3 and HL-13 have two and one consensus N-linked glycosylation sites, respectively (See Tables 3 and 4). These sites are conserved with those of XL-35, which has a total of three potential sites (FIG. 2). Hydropathy plots obtained using the Pepplot program of GCG indicated that each N-terminal portion of XL-35, HL-3, and HL-13 is composed of hydrophobic amino acids, which suggests the presence of the signal peptide sequence that causes proteins to enter the secretory pathway (FIG. 3).

The HL-3 and HL-13 cDNA clones were each expressed in E. coli to compare agglutination activities and carbohydrate-binding specificities with that of XL35 and to prepare antibodies.

Expression of human HL-3 and HL-13 coding sequences was performed using the same method for expression of XL-35. First, the sequences encoding HL-3 and HL-13 were modified by PCR to introduce a SalI restriction site at the predicted signal sequence cleavage site and a HindIII site at C-terminal end. These sequences were then cloned into the pQE-9 QIAexpress vector. HL-3 and HL-13 production in recombinant E. coli was induced with IPTG, and analysis revealed the expression of 34~35 kDa proteins. The recombinant HL-3 and HL-13 proteins were separately purified with $Ni^{++}$-NTA columns. Purification and renaturation carried out as for XL35. Similar to recombinant XL-35, the human recombinant lectins slowly precipitated if the urea concentration was decreased. The human recombinant lectins, however, required a higher concentration of urea for solution, 5 M, as compared to 2 M for XL35. The purified recombinant human lectin proteins were assayed for agglutination of trypsinized, fixed rabbit erythrocytes. The agglutination assays gave inconclusive results because of the high concentration of urea required to maintain the proteins in solution.

Figures 4A, 4B:
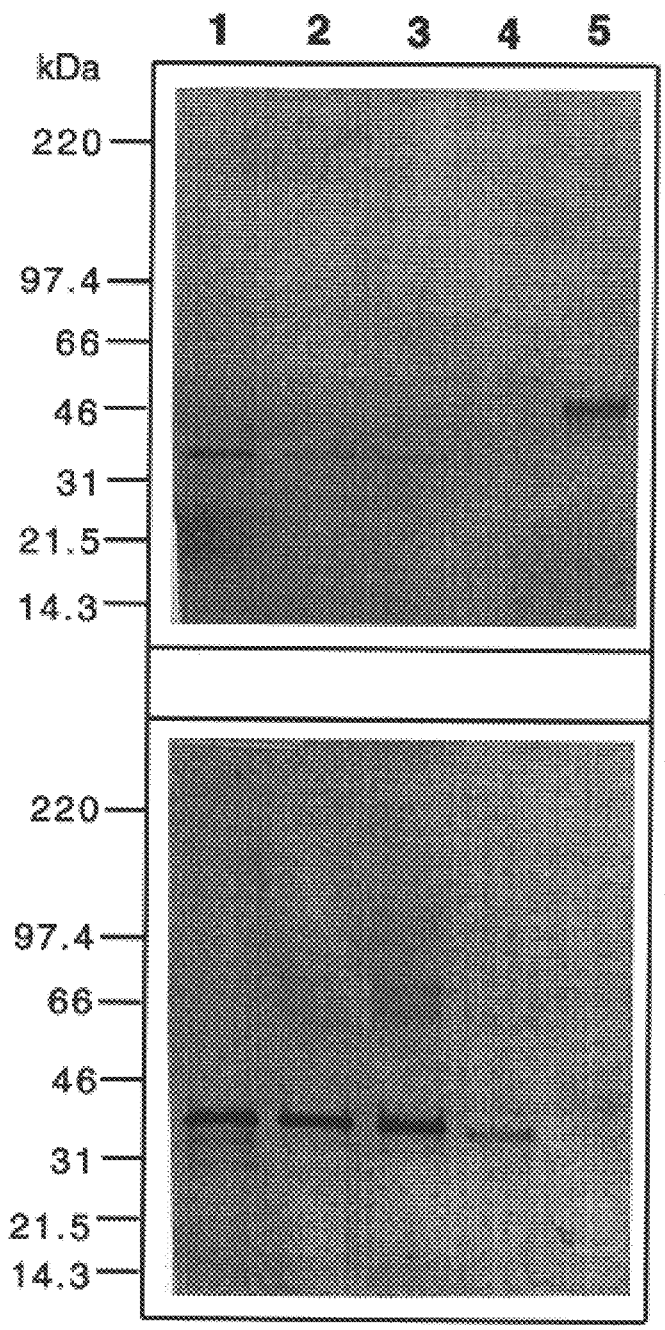
FIG. 4 illustrates immunoblot analysis of anti-XL35 and anti-recombinant XL35 antibody specificity. Partially purified bacterially expressed XL35 (lane 1), HL-3 (lane 2), HL-13 (lane 3), N-glycanase treated XL35 (lane 4, and XL35 (land 5) were resolved on 4–15% gradient gels by SDS-PAGE, and blotted to PVDF membrane. The proteins were detected by immunoblotting with anti-XL35 (Panel a) and anti-recombinant XL35 (Panel B) polyclonal antisera. Molecular weight standards are depicted at left.

Melibiose-purified native XL35, recombinant XL35, and recombinant HL-13 were separately injected into rabbits to prepare antisera. Anti-native XL35 antibody was more reactive in Western blots against affinity purified Xenopus oocyte lectin than N-glycanase treated XL35, recombinant XL35, HL-3 or HL-13 (FIG. 4). Conversely, anti-recombinant XL-35 and anti-recombinant HL-13 antibody was more reactive against the non-glycosylated than the native XL-35.

Figure 5:
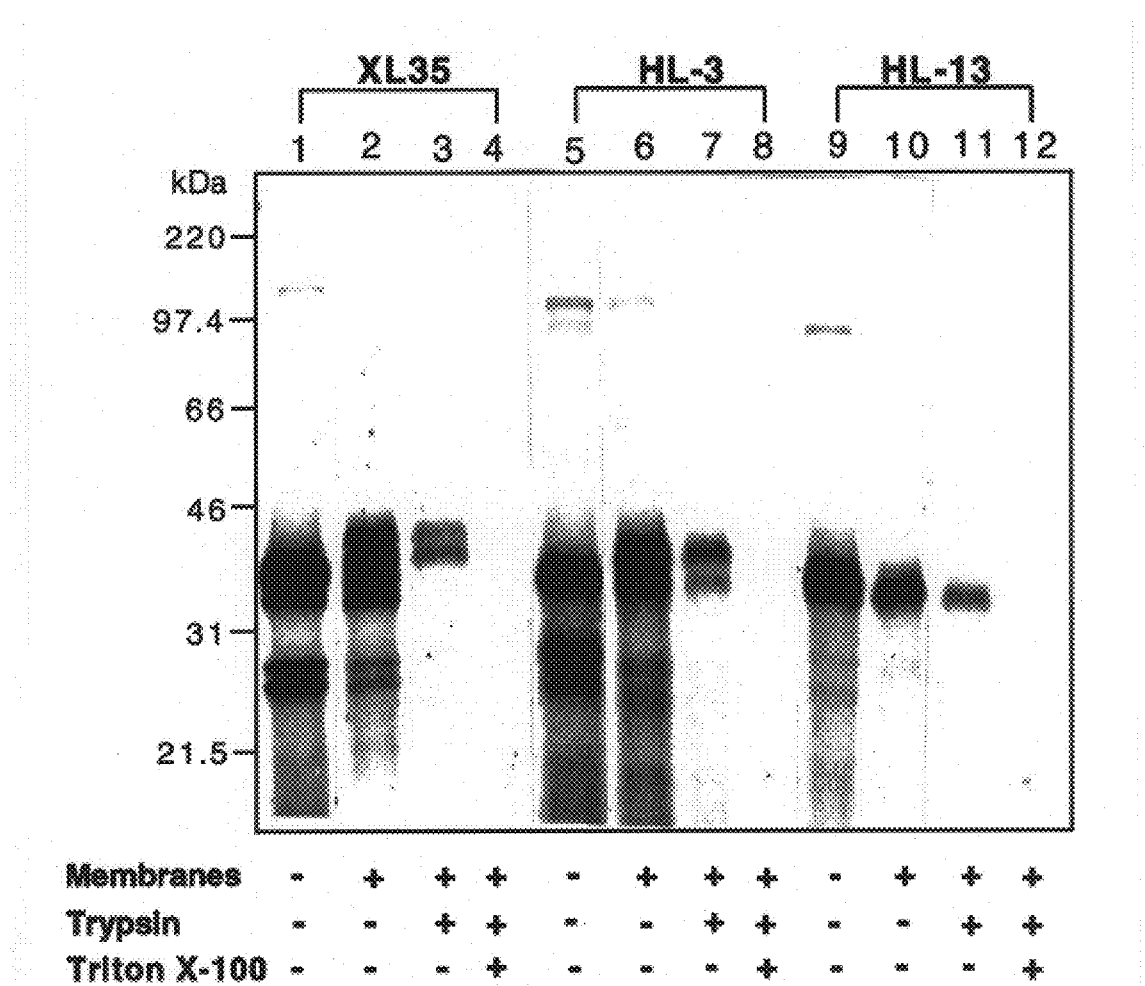
FIG. 5 shows in vitro translation of XL35, HL-3, and HL-13 cDNAs. Each cDNA was transcribed and translated in vitro using TNT T7 polymerase-coupled reticulocyte lysate system as described in the examples. In vitro translation was performed with or without microsomal membranes as indicated at the bottom of the figure. Aliquots from each translation product were then digested with trypsin in the presence of absence of Triton X-100 as indicated. Samples were separated by 4–15% SDS-PAGE and subjected to autoradiography. Molecular weight markers are indicated at the left of the figure.

The full length cDNA clones of XL35, HL-3, and HL-13 were transcribed/translated in vitro using a TNT T7 polymerase-coupled reticulocyte lysate system. A comparison of the translation products of XL35 in the absence and presence of microsomal membranes showed that two slightly higher molecular weight proteins were produced in the presence of microsomal membranes (lanes 1 and 2 of FIG. 5). This result indicates that different forms of glycosylated XL35 were produced in the presence of microsomal membranes. The deduced amino acid sequence of XL35 predicts three possible N-glycosylation sites at Asn residues 155, 164, and 218 (FIG. 2). Similarly, translation of HL-3 in vitro in the presence of microsomal membranes resulted in the glycosylation of the protein, evidenced by decrease in mobility upon SDS-PAGE (lanes 5 and 6 of FIG. 5). HL-3 contains two possible N-glycosylation sites at Asn 155 and 164 (Table 3). The in vitro translation products of HL-13 in the presence or absence of microsomal membranes were similar in size (lanes 9 and 10 of FIG. 5). HL-13 has one potential N-glycosylation site at Asn 166 (Table 4). HL-13 cDNA translated in vitro shows that the molecular weight of N-glycosylated and signal peptide-cleaved HL-13 (lane 10 of FIG. 5) is similar to HL-13 with the signal peptide intact HL-13 (lane 9 of FIG. 5). The net loss in molecular weight for the HL-13 translation product in the presence of membranes, compared to the molecular weight observed in the absence of membranes, indicates that the loss of signal peptide was not offset by glycosylation. Trypsin cleavage of the in vitro translation products in the presence of microsomal membranes did not alter the mobility of any bands but reduced somewhat the amount of the glycosylated forms of XL35, HL-3, and HL-13 (lanes 3, 7, and 11 of FIG. 5). The smaller in vitro-synthesized products of XL35 were fully sensitive to digestion. Trypsin digestion in the presence of Triton X-100, however, degraded all the in vitro translation products of XL35, HL-3, and HL-13 (lanes 4, 8, and 12 of FIG. 5). These results indicate that XL35, HL-3, and HL-13 all enter the secretory pathway and are post-translationally modified.

To examine the carbohydrate-binding activity of the in vitro-translated products, all in vitro translation products were applied to a column of immobilized melibiose in the presence of $Ca^{2+}$ or EDTA. The glycosylated forms of XL35 bound to melibiose in the presence of $Ca^{2+}$ but not in the presence of EDTA. XL35 translated without membranes did not bind to melibiose, however. These results indicate that only XL35 translated with membranes can bind to melibiose in the presence of $Ca^{2+}$, suggesting that signal sequence cleavage and/or N-glycosylation are required for binding activity. Bacterially expressed and renatured XL-35, however, showed a low level of erythrocyte agglutination activity in the presence of 2 M urea. Without wishing to be bound by any particular theory, it is believed that these differences are caused by the presence or absence of signal peptide sequence and/or glycosylation in the lectins used in these assays. The bacterially-expressed active XL35 did not contain the signal peptide sequence, and there is a possibility that the presence of signal peptide sequences caused a change of tertiary structure. Furthermore, recombinant bacterial products lack glycosylation. Interestingly, no in vitro translation products of HL-3 and HL-13 bound to melibiose. These results indicate that the human homologs of XL35 have different carbohydrate-binding specificities from that of XL35.

This conclusion is also supported by the results of the melibiose binding assay with the lectin-related protein in rat heart preparation that is most likely homologous to HL-3. The crude lectin was extracted from rat heart using as described in the Examples herein [See also Roberson, 1982 supra] and applied to a melibiose affinity column. The binding ability to melibiose was analyzed by Western blotting using anti-XL35 antibody. The rat crude heart lectin-related protein did not bind to the melibiose column, demonstrating again that the human and rodent lectin-related proteins do not bind to the same oligosaccharide ligands as XL35.

The advantages of genomic DNA screening in a P1 vector are the large insert size of these clones (50–100 kb), significantly increasing the chances of obtaining the entire gene, and the rapid screening time of the arrayed library. A comparison of the sequences of the HL-3 and HL-13 cDNAs revealed that their DNA sequences were 84% identical at the DNA level and 85% identical at the amino acid level (Tables 3–4 and FIG. 2). Primers were designed to regions of the HL-3 and HL-13 cDNAs whose nucleotide sequences were distinct from each other (9/25 and 19/25 mismatches, respectively; boxed sequence shown in Tables 3 and 4). These primers produced clearly unique 161 bp PCR products (dotted sequences shown in Tables 3 and 4) with each cDNA sequence upon amplification with human genomic DNA. These primer pairs were then used for genomic DNA screening and also used directly for chromosomal mapping. Two genomic clones containing HL-3 and HL-13 were isolated. A comparison of the partial DNA sequences of these genomic clones indicated that the HL-3 and HL-13 genes each have at least one intron that differ in size and location. Moreover, PCR reactions from several combinations of synthetic primers and each genomic clone revealed different size of products. These results indicate that HL-3 and HL-13 cDNA clones are different gene products. Each genomic clone was then used directly for chromosome localization by FISH analysis.

Table 3 provides the nucleotide and deduced amino acid sequence of HL-3. The N-terminal sequences are underlined. The heart EST sequence that was used as a probe for cDNA screening is underlined. The probe sequences used for Northern blot analyses are denoted by a dotted sequence. The boxed sequences are the primers used for chromosomal localization and screening of each genomic cDNA clone. Asterisks below the peptide sequence indicate the potential N-glycosylation site(s).

Table 4 provides the nucleotide and deduced amino acid sequence of HL-13. The N-terminal sequences are underlined. The heart EST sequence that was used as a probe for cDNA screening is underlined. The probe sequences used for Northern blot analyses are denoted by a dotted sequence. The boxed sequences are the primers used for chromosomal localization and screening of each genomic cDNA clone. Asterisks below the peptide sequence indicate the potential N-glycosylation site(s).

The primer pairs that produced unique 161 bp PCR products with the HL-3 and HL-13 genomic DNA clones were next used for chromosomal mapping. PCR using these probes and hamster genomic DNA or mouse genomic DNA as template showed no products. DNA from a human/hamster somatic cell hybrid panel was tested for the amplification of the 161 bp HL-3 and HL-13 fragments using the gene specific primer pairs that were used for genomic DNA screening. Cell lines that scored positive for the HL-3 and HL-13 fragments were all found to contain human chromosome 1. Each other chromosomes were excluded as the site for HL-3 or HL-13 genes by discordancies in at least 23 of the hybrid cell lines. To analyze the sub-localization of the HL-3 and HL-13 genes, separate FISH (fluorescence In situ hybridization) analyses were performed using genomic clones encoding HL-3 and HL-3 as probes. Human chromosomes were hybridized with the HL-3 or HL-13 probe and the control probe which was known to map to 1p34. Measurements of the distances between the probe control and the fluorescent signal from the HL-3 or HL-13 probes demonstrated that the HL-3 and HL-13 genes are located at positions which are 18% and 16%, respectively, of the distance from the heterochromatic-euchromatic boundary to the telomere of chromosome 1q, an area that corresponds to band 1q23. A total of 80 metaphase cells were analyzed for each HL-3 and HL-13 probe hybridization and 71 cells for HL-3, 68 cells for HL-13 exhibited specific labeling. In summary, the HL-3 and HL-13 genes are both located at chromosome 1q23 and are in close proximity. They are most likely separated by at least 50 kb since they are not located in the same P1 clone.

The genes that encode all known selectin family members (L-, E-, and P-selectin) are found between 1q22 and 1q25 [Watson et al. (1990) *J. Exp. Med.* 172, 263–272]. Therefore, this locus has been designated an 'adhesion molecule locus' [Tedder et al. (1989) *J. Exp. Med.* 170, 123–33]. Most genes encoding pentraxin, which are involved in immune- or inflammation-associated functions, are also located at chromosome 1q23.

Figure 6A:
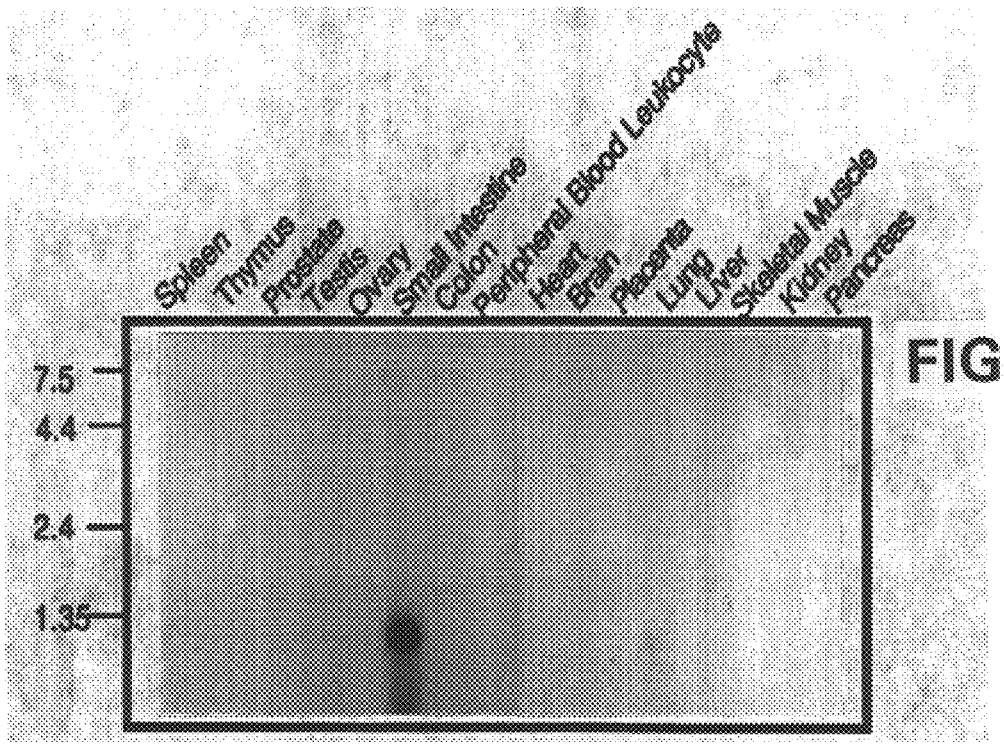
FIGS. 6A–6B illustrate tissue distribution of HL-13 and HL-3 mRNA transcripts. A Northern blot of human tissue poly(a) RNAs was hybridized with radiolabeled specific probes for HL-13 (FIG. 6A) or HL-3 (FIG. 6B). The 161 bp amplimers (dotted-line sequences of FIG. 6) were obtained from specific primers for HL-3 and HL-13 (boxed sequences of Table 4). Each 161 bp specific probe had 58/161 mismatches.
Figure 6B:
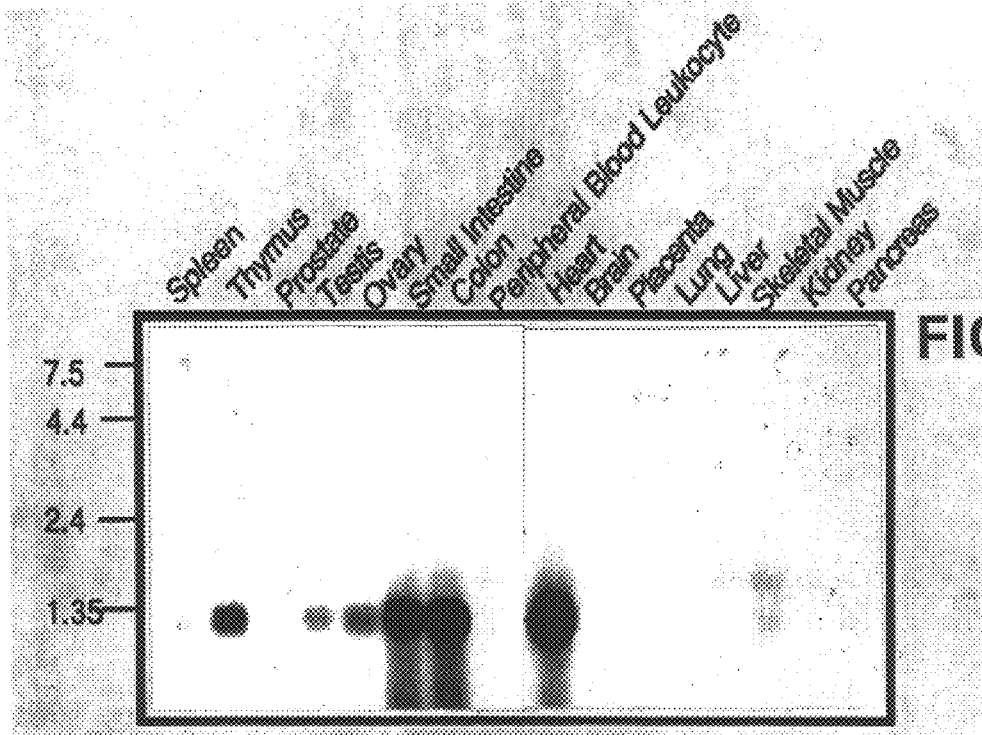

The transcript levels of HL-3 and HL-13 were determined by Northern blot analysis using as radiolabeled probes the same 161 bp amplimers used in the chromosomal localization experiments. These fragments are distinct from each other (58/161 mismatches in nucleotide sequences, Tables 3 and 4). The major transcripts of HL-3 and HL-13 were 1.3 kb in length. The transcript of HL-3 was most abundant in heart and found in high levels in colon, small intestine, and thymus, with lower levels in ovary, testis, and spleen. A few other tissues show very low levels of expression: skeletal muscle and placenta (FIGS. 6A–6B). A minor band of 1.6 kb for the HL-3 transcript was barely detectable in liver, skeletal muscle, testis, peripheral blood leukocytes, small intestine, and colon. Preliminary results indicate this 1.6 kb band represents an intron splicing variant. By contrast to HL-3, the 1.3 kb transcript of HL-13 was detectable only in small intestine. HL-13 appears to be more abundant than HL-3 in small intestine, because 6 of 7 clones isolated from the small intestine cDNA library contained HL-13 cDNA sequences.

Immunohistochemistry was performed with human colon, thymus, and heart tissue sections to determine which cell types expressed HL-3. Striking results were obtained from colon and thymus sections using anti-XL35 primary antibody and peroxidase conjugated secondary antibody. The lectin-related protein specifically and intensively stained epithelia lining the blood vessels in colon and thymus tissues. Surprisingly, the labeling appeared throughout the endothelial cells, not just adsorbed to the surface. The vessel endothelial cells of colon were stained with high intensity. This result was consistent with the relatively abundant transcripts observed in tissue Northern blot analyses (FIGS. 6A–6B). Endothelial cells express many kinds of cell adhesion molecules involved in the adhesion of platelets and leukocytes. The endothelial cell expression and chromosomal localization of HL-3 suggests strongly that the human homologs of XL35 function as adhesion molecules, perhaps in thrombosis or inflammation.

In heart sections, the lectin-related protein shows weak staining intracellularly in the cardiac myocytes. The endocardium, developed from endothelium was also reactive. The signal in heart blood vessel endothelial cells, however, showed very intense staining, much stronger than for the cardiac myocytes.

Figure 7:
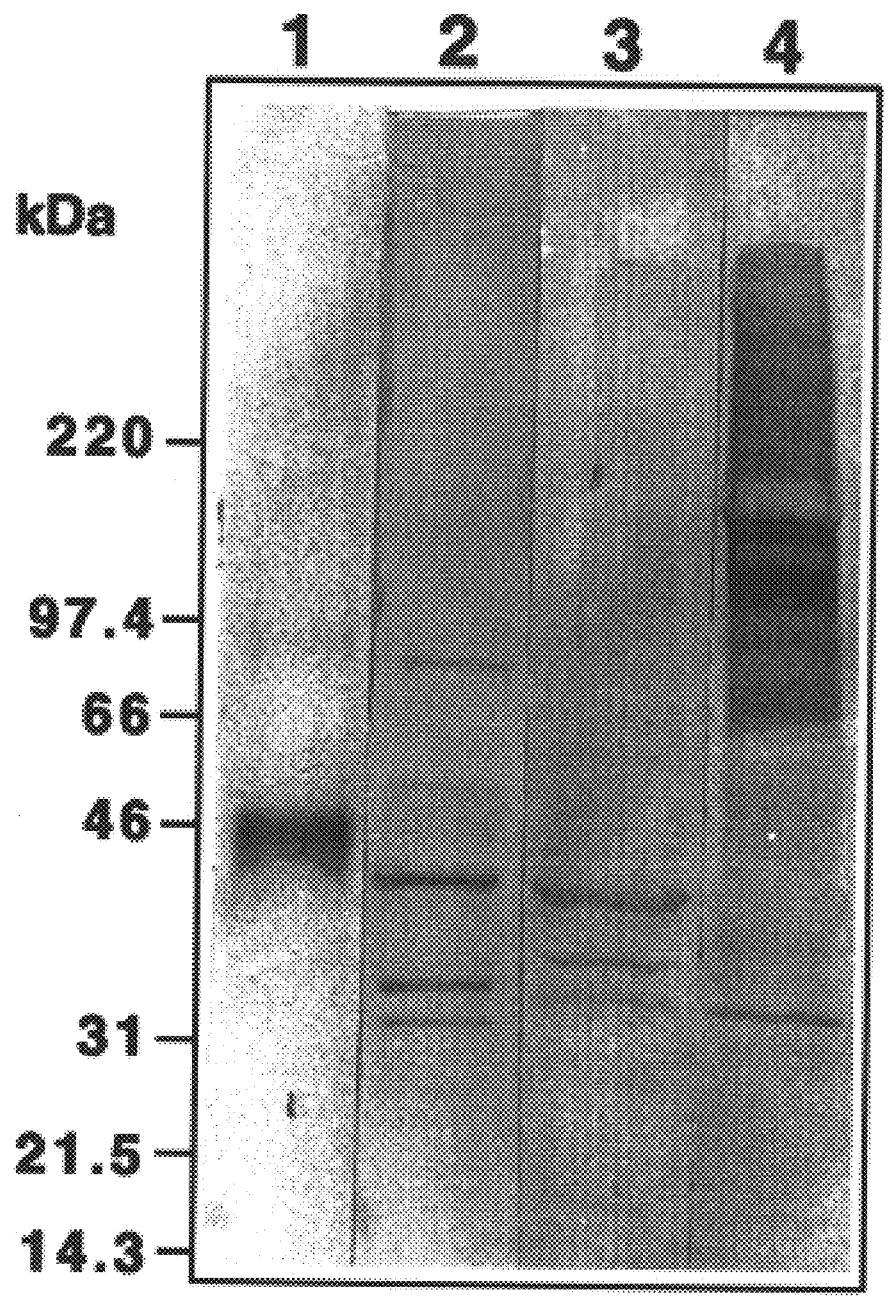
FIG. 7 shows immunoblot analysis of rat, mouse, and Xenopus aevis heart using anti-XL35 Ab. Tissues were extracted as described in the examples. Total 400 μg of each extract was resolved by SDS-PAGE on 4–15% gradient gels and detected by immunoblotting with anti-XL35 polyclonal antisera. Lane 2, rat heart extract; lane 3, mouse heart exact; lane 4, Xenopus laevis heart extract. Purified Xenopus laevis oocyte lectin (XL35) was also immuno-blotted as a standard in lane 1. Molecular weight markers are indicated at the left of the figure.
Figure 8:
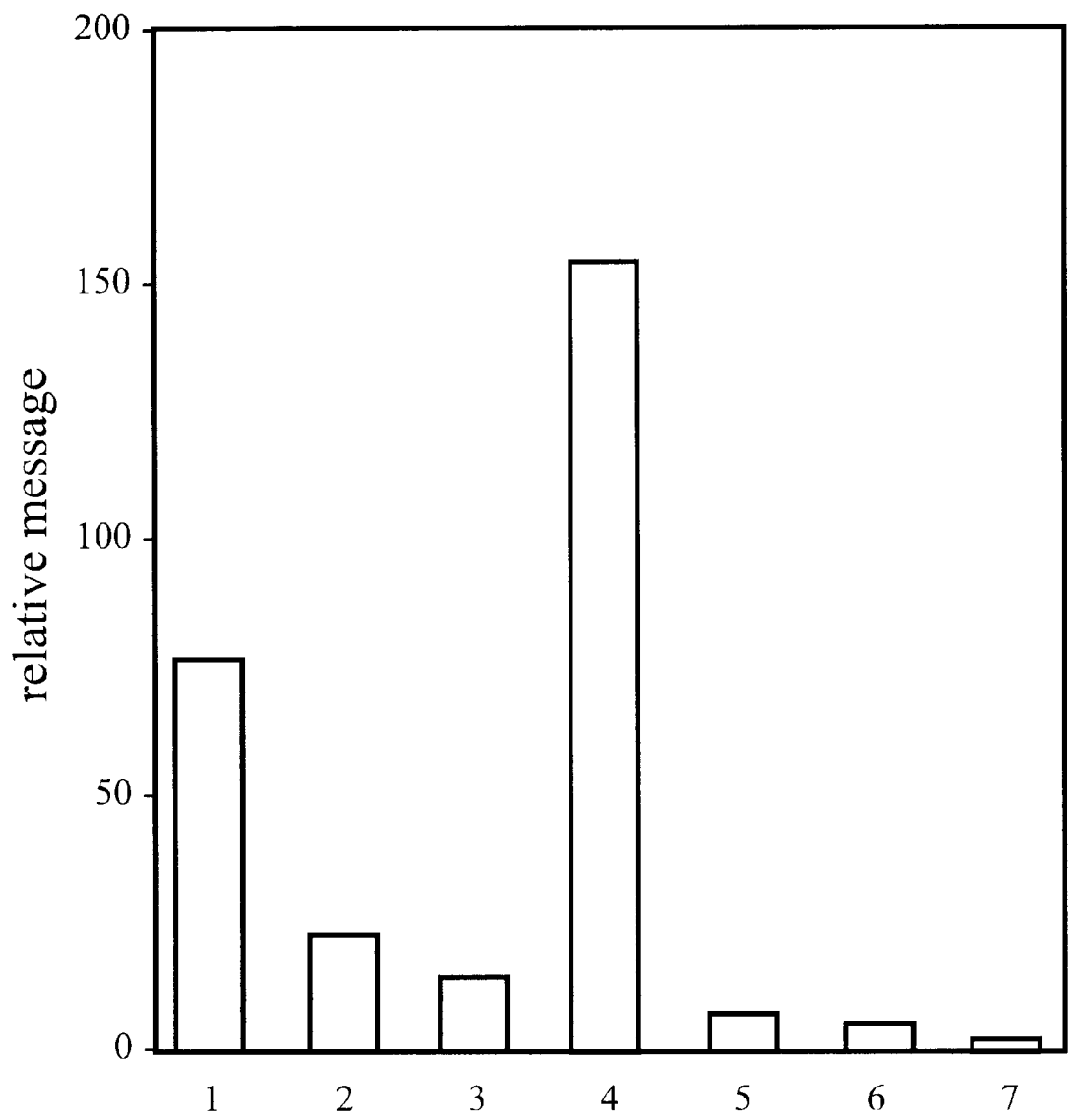
FIG. 8 illustrates the results of Northern blot analysis of total RNA (20 μg/lane) from oocyte or embryos at various stages: lane 1, stage VI oocytes; lane 2, cleavage stage embryos; lane 3, blastula; lane 4, late glastrula; lane 5, late neurula; lane 6, hatching embryos; lane 7, tadpole. The blot was hybridized with the 401 pb lectin restriction fragment as the radiolabeled probe. Densitometer values obtained from the Northern blot were normalized to the values obtained when the same blot was probed with a mitochondrial rRNA fragment (Yost et al., 1995).

Mouse, rat, and *Xenopus laevis* hearts were extracted and analyzed by Western blotting using anti-XL35 antibody as described in Examples hereinbelow. Heart tissue was chosen because HL-3 transcripts are highly expressed in heart tissues based on Northern blot analysis. Western blot results from rat and mouse heart extracts showed similar bands except for a protein band at 70–80 kDa in rat heart (FIG. 7). Three protein bands were detected at molecular weights between 33–40 kDa in both rat and mouse hearts (FIG. 7). These sizes are similar to the calculated molecular weight of HL-3. The heterogeneous sizes of HL-3 in rat and mouse hearts suggest different glycosylated forms. The exceptional protein band (70–80 kDa) from rat heart suggests the possibility of another lectin homolog. The *Xenopus laevis* heart extract subjected to Western blotting with anti-XL35 antibody showed four major bands of around 34, 69, 100, and 140 kDa (FIG. 7). Barondes reported that the serum from estrogen-induced *Xenopus laevis* contained a 69 kDa protein that was weakly reactive against anti-XL35 antibody. This protein also bound to melibiose-agarose in a $Ca^{2+}$ dependent manner, and peptide mapping analysis showed some similarity with XL35 [Roberson et al., 1985 supra].

Rat heart extract was applied to a melibiose-agarose column in the presence of $Ca^{2+}$ and the binding pattern was analyzed by Western blotting using anti-XL35. No lectin-related proteins bound to the melibiose column, indicating that the carbohydrate-binding specificity of the rat lectin-related protein is different from that of XL35. This results was consistent with that of the melibiose column binding assay using in vitro translation products.

SVEC cells, an SV-40 virus transformed mouse lymph node endothelial cell line, were lysed and analyzed by Western blotting using anti-XL35 antibody. Three different protein bands were detected with sizes of 35, 44, and 47 kDa in sizes. To determine the location of the lectin-related protein in endothelial cells, SVEC cells were studied by immunofluorescence and confocal microscopy. The cells were stained with anti-XL35 antibody and visualized by FITC-conjugated anti-goat rabbit IgG in the presence and absence of saponin to distinguish cell surface and intracellular locations. The non-permeabilized SVEC cells showed very low levels of labeling on cell surfaces. The SVEC cells permeabilized by saponin, however, showed strong fluorescence intracellularly highlighted by the presence of distinct labeled vesicles. These immunofluorescence labeling results demonstrate that the lectin-related protein is contained in the secretory pathway and is stored in secretory vesicles. Permeabilized SVEC cells stained with pre-immune sera showed extremely low levels of labeling. The permeabilized B16 cells, a mouse melanoma cell line, showed the same very low level of staining as those stained with pre-immune sera.

In summary, the results of several experiments indicate the HL-3 and HL-13 function as lectins: (1) They are 60% identical and 74% similar in amino acid sequences to the known Xenopus lectin XL35, showing large stretches of completely identical sequences; (2) The genes encoding HL-3 and HL-13 are located at chromosome 1q23, a site known as the endothelial adhesion molecule locus; (3) The lectin-related proteins are localized almost exclusively in blood vessel endothelial cells, only in a unique set of tissues; (4) A homologous lectin-related protein is expressed in a cultured lymph node endothelial cell line and is localized in large storage vesicles.

Tables 2A–2B illustrate the results of a TBLAST search with XL35 cDNA sequences. The DNA sequence encoding XL35 was used to search for DNA sequence and protein sequence similarity. The human heart-expressed sequence tag (EST), 251 bp, was found in GenBank sequence database using TFASTA and TBLAST searches (Table 2A). This sequence (Genbank, Z36760) showed 74% identity at the DNA sequence level and 83% identity at the amino acid level with that of XL35. The subject sequence indicates the deduced amino acid sequence from human heart EST sequence. Table 2B represents the DNA sequence of the heart EST sequence. The primers (underlined sequence) were designed for PCR reaction with human placenta, liver, and thymus cDNA as templates and the amplimer was used for screening cDNA libraries for human homologs of XL35.

The nucleotide sequence encoding HL-3, including the signal peptide, is given in SEQ ID NO:3, nucleotides 107 to 942, and the deduced amino acid sequence for the mature protein is given in SEQ ID NO:4. Nucleotides 305 to 554 of SEQ ID NO:3 correspond to a human EST of previously unidentified function (Genbank, Z36760); a probe of this sequence was used to screen a human cDNA library for lectin sequences.

The nucleotide sequence encoding HL-13, including its signal peptide, is given in SEQ ID NO:5, from nucleotides 31 to 1018, and the deduced amino acid sequence is given in SEQ ID NO:6. One predicted N-glycosylation site is at amino acid 137 of the mature HL-13 protein. The portion of the sequence corresponding to human EST (Genbank Z36760) occurs at nucleotides 235–484, and a probe of this sequence was used to screen a human cDNA library for lectin clones.

FIG. 3 illustrates hydropathy plots of XL35, HL-3, and HL-13. Each was obtained from deduced amino acid sequences using the pepplot program of the University of Wisconsin Genetics Computer Group (GCG software). The hydrophobicities were calculated by Hopp-Woods' (dotted line) and Kyte-Dolittle's (solid line) method. Each N-terminal end of XL35, HL-3, and HL-13 has hydrophobic amino acid residues indicating a signal peptide sequence. None of the three lectins has a predicted transmembrane domain.

Fluorescence in situ hybridization (FISH) using HL-3 and HL-13 genomic probes to human chromosomes was used to localize the genes encoding HL-3 and HL-13 to the 1q23 locus by measuring relative distances from the control probes. The control mapped to 1p34.

Immunofluorescence staining of endogenous lectin in cultured SVEC cells was carried out by incubating SVEC cells with anti-XL35 in the presence or absence of saponin. SVEC cells incubated with pre-immune serum served as controls. B16 mouse melanoma cells were also incubated with anti-XL35. Antibody binding was detected by FITC-coupled secondary antibody binding and visualized by Confocal Fluorescence microscopy. The results show that there was a major band at about 35 kDa and two minor bands at 44 and 47 kDa. Without wishing to be bound by any particular theory, it is believed that these bands represent different glycosylated forms of HL-3. Immunofluorescence microscopy revealed that the HL-3 is found within intracellular vesicles.

We have expressed and further characterized XL35, then isolated cDNAs from human sources which show similar sizes to XL35, as well as high degrees of identity (60% at the amino acid level). Rodent homologs have been detected in mouse and rat tissue using Western blots. These results demonstrate that a family of lectin-related proteins with significant similarity to XL35 exists in vertebrates, and suggest that members of this family perform physiological functions in adult organisms as well as in *Xenopus oocytes* and embryos. The amino acid sequences of these human lectin-related proteins are distinct from any of the groups previously described, demonstrating the presence of an additional unique family of animal lectins.

The African clawed toad, *Xenopus laevis*, contains several lectins that are expressed in adult tissues and at various stages of embryonic development. The XL35 is stored in cortical granules where it accounts for 77% of the granule contents in association with trypsin and chymotrypsin-like proteases [Lindsay, 1989, supra]. Release of the lectin is believed to contribute to the transformation of the fertilization envelope that blocks sperm penetration and subsequent polyspermy [Zalik, 1991, supra].

We isolated and characterized cDNA clones encoding XL35 (SEQ ID NO: 1). We used melibiose [Galα1→6Glc] affinity chromatography to isolate the oocyte lectin (monomer molecular masses of about 45 and 43 kDa). XL35 forms multimers of about 500 kDa and this multimerization is mediated by disulfide bonds. After obtaining internal peptide sequences, full length cDNAs were isolated from an ovary λgt11 library that encoded a protein of 313 amino acids with three potential N-linked oligosaccharide sites (see SEQ ID NO:2). XL35 activity is assayed by agglutination of trypsinized, fixed rabbit erythrocytes [Roberson, 1982 supra], although its endogenous ligands are found in egg jelly. Recently, Quill et al. purified a candidate of XL35 ligands, which was O-linked glycoprotein. They observed that α-galactoside residues of the glycoprotein are an essential carbohydrate moiety recognized by XL35. A recent NMR study of oligosaccharides present in Xenopus egg jelly [Strecker et al. (1995) *Glycobiology* 5, 137–46] demonstrated large amounts of O-linked oligosaccharides terminating in the sequence: Galα(1,4)[Fucα(1,2)]Galβ(1,3)GalNAc—, which is most likely the endogenous ligand for XL35, based on the inhibition of the erythrocyte agglutination reaction with various disaccharides and a recent study of the egg jelly ligand. The erythrocytes themselves have significant amounts of the glycolipid termed globoside: Galα(1,4)Galβ(1,3)Glc-ceramide, which is most likely the ligand for XL35 on the erythrocytes. This agglutination activity requires calcium and can therefore be inhibited by EDTA. Many animal lectins have been shown to require calcium ions for activity and a C-type lectin sequence motif for the calcium-binding site of these lectins has been defined [Drickamer, 1993, supra]. The XL35 sequence, however, does not contain the sequence motif defined for most previously characterized "C-type" lectins. Another class of lectin, the pentraxins require $Ca^{2+}$ for their carbohydrate-binding activity but do not contain "C-type" motif in their sequences.

An XL35 clone lacking the signal peptide sequence and encoding 6 histidine residues at the N-terminus of the protein was expressed in *E. coli*. The activity in the presence of 2 M urea of the bacterially expressed XL35 was completely inhibited by EDTA and melibiose. The results from these experiments, therefore, demonstrate that the recombinant XL35 displays properties like those of the native lectin purified from oocytes and that the cDNA does indeed encode the oocyte lectin.

The Northern blot analysis of XL35 in developing embryos of *Xenopus laevis* is consistent with the results of two previous studies which demonstrated significant amounts of a lectin with similar structure and specificity to the oocyte lectin in blastulae [Roberson, 1982 supra], and which used a polyclonal antibody to the oocyte lectin to localize cross-reacting material to the blastopore region and to extracellular locations on the roof of the blastocoel [Outenreath, 1988, supra].

The nature of the glycoconjugate ligands of XL35 in the embryo is unknown, although there are recent reports of a blood group-B active determinant expressed on glycoconjugates on *Xenopus blastulae*. These determinants are expressed in areas of cell-cell contact, and it seems very possible that XL35 or lectins similar to it could be binding to these glycoconjugates and regulating intercellular adhesion in the embryo [Nomura, 1995, supra]. Structural analyses of the oligosaccharide ligands of the lectin, as well as in situ hybridization and immunocytochemical experiments to refine the locations of the lectin biosynthesis and secretion are in progress to investigate this hypothesis. In situ hybridization was carried out using *Xenopus oocyte* and embryos at various stages; the results indicate that a specific area of endoderm is stained during gastrulation. Although the ligand (s) of XL35 in the embryo is not known, it is believed that XL35 binds to glycoprotein, glycolipid or GPI anchored protein(s) with α-galactoside.

Immunoblots of Xenopus heart extracts using anti-XL35 antibody revealed bands at 34, 69, 100, and 140 kDa. The 34 kDa band is believed to be a form of XL35 and the 69 kDa band a related lectin described by Roberson et al. [Roberson, 1985, supra]. The function and source of the adult serum form (69 kDa) are not known, but the adult XL-69 form does agglutinate rabbit erythrocytes. Agglutination, as well as binding to immobilized melibiose, can be inhibited by EDTA, while compositional analysis indicates that the lectin contains bound calcium. The 69, 100, and 140 kDa proteins from Xenopus heart also bind to melibiose.

The derived DNA and peptide sequences of XL35 were used to search protein and DNA sequence databases, and a single entry was identified from non-Xenopus sources. The sole sequence match was a fragmentary 251 bp cDNA sequence obtained from a human heart cDNA library (GenBank accession number Z36760, Tables 2A–2B as an expressed sequence tag (EST). Using the human EST sequence to design oligonucleotide primers, an amplimer was obtained from human liver, spleen, and placenta cDNA sources that was essentially identical to the human heart cDNA sequence in the database. The amplimer was used to probe Northern blots of various human tissue RNAs and the highest signal was an approximately 1.3 kb mRNA obtained from heart and small intestine. The amplimer was used to probe a human heart cDNA library and clones were isolated that encode two homologs of XL35, termed HL-3 and HL-13 (See SEQ ID NOS:3–6).

At the amino acid level, the two human lectin-related proteins, HL-3 and HL-13 show 60% and 56% identity with XL35, respectively (FIG. 2). The amino acid sequence identity between HL-3 and HL-13 is 83% (88% similarity). These calculations include the signal peptide sequences which have very distinctive sequences (FIG. 2). Calculation of the identities between human lectin-related proteins and XL35, or between HL-3 and HL-13 is increased if these signal sequences are not included in the calculation. The possible N-glycosylation site(s) of XL-35 (three sites), HL-3 (two sites), and HL-13 (one site) are perfectly conserved (Tables 3 and 4). These three lectin-related proteins also have highly conserved cysteine residues (9 out of 10) which might mediate the multimerization form of XL35. Sequence data from cDNA and deduced amino acid sequences strongly suggest that HL-3 and HL-13 are human homologs of XL35.

cDNAs encoding full length HL-3 and HL-13 were expressed in E. coli with the N-terminal 6 histidine tag and without signal peptide sequences using the same methods as for XL35 expression. Erythrocyte agglutination assays with HL-3 and HL-13, however, gave no conclusive results because of the high concentration of urea need to retain HL-3 and HL-13 solubility. Purified HL-13 was injected (in the presence of urea) into a rabbit to prepare antibody.

Immunoblot analysis from mouse and rat heart extracts using anti-XL35 indicate the presence of rodent homologs of XL35 that have similar sizes to XL35 and the human homologs. Bands of different sizes (33–40 kDa) are believed to indicate differentially glycosylated forms. It is not clear why rat heart extract contained one exceptional band at 70–80 kDa compared to that of mouse. We obtained a partial cDNA sequence of the mouse homolog to HL-3 using PCR with mouse heart cDNA and primers that designed based on HL-3 cDNA sequences. The partial mouse cDNA sequences are 461 bp in length and showed 77%, 79%, and 61% amino acid sequence identity with HL-3, HL-13, and XL35, respectively.

In vitro translation of XL35, HL-3, and HL-13 cDNA clones confirmed that the translation products are glycosylated in a system capable of performing that post-translational modification. Melibiose binding assays with each of the in vitro translation products showed that only the glycosylated form of XL35 bound to the melibiose. None of in vitro translation products bound to melibiose, indicating that the carbohydrate-binding specificities of HL-3 and HL-13 differed from that of XL35. The lectin-related proteins prepared from rat heart extract also did not bind to melibiose.

Analysis of the human lectin-related protein transcript expression by Northern blotting using the specific 161 base pair probes for HL-3 and HL-13 demonstrated different levels of 1.3 Kb transcript expression depending on the tissue probed. HL-13 was specifically expressed only in small intestine. The HL-3 transcript was expressed in many tissues: heart>colon>small intestine>>thymus>ovary>testis>spleen>skeletal muscle>placenta (FIG. 6A). Only small intestine tissue expressed both HL-3 and HL-13 (FIGS. 6A–6B). A very faint band of 1.6 kb was detectable using the HL-3 specific probes in some tissues. It is not clear if this transcript is another homolog form or simply a invariant splicing product, or possibly non-specific signal. Human colon, thymus, heart, lung, and kidney tissue sections were subjected to immunohisto-chemistry using anti-XL35 antibody. The endothelial layer of blood vessels in colon and thymus was specifically and strongly stained. In heart tissue, blood vessel endothelial cells were also strongly stained, the endocardium layer, derived from endothelial cells, also stained, and the cardiac myocytes showed weak staining. These results were consistent with those of Northern blots with various human tissues (FIGS. 6A–6B). From the combined results from Northern blots and immunohistochemistry, the human lectin-related proteins are expressed in some but not all endothelial cells; ie, they show considerable tissue specificity.

The SVEC cell is an endothelial cell line derived by SV40 (strain 4A) transformation of endothelial cells from lymph node vessels from an adult male C3H/HeJ mouse. SVEC cells were lysed and analyzed by immunoblot using anti-XL35. Strikingly, a major band of around 35 kDa and two minor bands of 44 and 47 kDa were detected by anti-XL35 Ab; the main bands are believed to be different glycosylated forms of HL-3. Immunofluorescence microscopy of SVEC cells using anti-XL35 Ab in the presence of saponin indicated that the lectins were present primarily intracellularly in vesicles.

The vascular endothelium has critical involvement in blood coagulation and in the inflammatory process. Endothelial cells contain specialized secretory organelles called Weibel-Palade bodies, which store and secrete von Willebrand factor (vWF, an adhesive glycoprotein involved in the formation of the platelet plug) [Wagner et al. (1982) J. Cell Biol. 95, 355; Wagner, D. D. (1990) Annu. Rev. Cell Biol. 6, 217] and P-selectin (for review see Bonfanti et al. (1989) Blood 73, 1109]. When endothelial cells are stimulated by agonists such as thrombin, histamine, complement components C5b-9, $Ca^{2+}$ ionophores, and other agents that elevate intracellular $Ca^{2+}$, Weibel-Palade bodies undergo exocytosis: vWF is released, and P-selectin is translocated to the cell surface. Thus, Weibel-Palade bodies are critical players in primary thrombosis, as well as in the early steps of inflammation. However, in SVEC cells, the XL35-like polypeptide is not found in Weibel-Palade bodies. These cells can secrete the lectin-related proteins when stimulated by an as yet unidentified signal; for example, cytokines or other agonists bound to a receptor on the cell cause release of the vesicles just as fertilization causes release of the contents of the cortical granules. For example, GlyCAM-1 is a ligand of L-selectin secreted by high endothelial venules (HEV) which binds to lymphocytes and promotes activation of β1 and β2 integrins. It thus qualifies as an activation/triggering molecule in the binding of lymphocytes to HEV. Immunohistochemical mapping of GlyCAM-1 at the EM level has showed it was stored in HEV intracellular organelles in the biosynthetic pathway including large cytoplasmic vesicles. There was no detectable staining on the cell surface of HEV endothelial cells. GlyCAM may be an appropriate model for the mechanism and function of the human lectin-related proteins (HL-3 and HL-13).

Genomic clones of HL-3 and HL-13 were used to analyze gene regulation and chromosomal localization of HL-3 and HL-13. The partial sequence data of each genomic clones and PCR reaction indicated that these two human lectin-related proteins are different gene products. FISH analysis showed that the HL-3 and HL-13 genes are located on chromosome 1q23. The region of human chromosome 1q22 to 1q25 contains genes that encode proteins with immune- and inflammation-associated functions [Tedder, 1989, supra]. These proteins include the all the known selectin genes and pentraxin genes including C-reactive protein (CRP), serum amyloid P (SAP), and a CRP pseudogene (CRPP1) [Walsh et al. (1996) *Immunogenetics* 44, 62–69; Watson, 1990, supra]. Pentraxins are lectins that most likely mediate a non-specific uptake of bacteria and cell debris that may be associated with inflammation and the immune responses [Pepys and Baltz (1983) *Adv. Immunol.* 34, 141–212]. These observations prompted the suggestion that selectins, pentraxins, HL-3, and HL-13 genes are very closely linked sequences that most probably arose via gene duplication events. Although also encoded at this locus, the HL-3 and HL-13 do not exhibit significant sequence homology with any of the selectins or pentraxins.

In summary, combined data from Xenopus, human, mouse, rat heart, and SVEC cells indicate that a family of lectins with amino acid sequence similarity to XL35 exists in vertebrates, and that members of this family perform physiological functions in adult organisms as well as in *Xenopus oocytes* and embryos. Their chromosomal localization, expression in the endothelial cells of some but not all tissues, and the intracellular location in SVEC cells all strongly suggest that the new family of vertebrate lectin-related proteins have important immunological functions, such as binding with immune cells or recognition of foreign cells, like selectins or pentraxins, or they can be involved in platelet adhesion and thrombosis. Moreover, the presence of several conserved cysteine residues among XL35, HL-3 and HL-13 points to a critical role of these cysteine residues in the structure and function of these lectins.

To define the biological functions of these new family of lectin-related proteins, further studies are carried out to examine the structure, specificity and ligands for the mammalian homologs of XL35, and to test the hypothesis that they function in intercellular adhesion. To determine the regulatory elements for the expression of these proteins, upstream promoter elements are identified from the genomic clones already isolated. To aid in the definition of their in vivo functions, animals deficient in the proteins are generated. Murine models for deficiencies in these lectin-related proteins are generated by standard gene ablation techniques. These mouse knockout models allow confirmation of the in vivo function of each of the lectin-related protein gene family members.

It is well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in Atlas of Protein Sequence and Structure, Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Polyclonal and/or monoclonal antibodies capable of specifically binding to a C-type lectin of the present invention are provided. The term antibody is used to refer both to a homogenous molecular entity, or a mixture such as a serum product made up of a plurality of different molecular entities. Monoclonal or polyclonal antibodies specifically reacting with the C-type lectins of the present invention can be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York. Also, recombinant immunoglobulins may be produced by methods known in the art, including but not limited to, the methods described in U.S. Pat. No. 4,816,567. Monoclonal antibodies with affinities of $10^8$ $M^{-1}$, preferably $10^9$ to $10^{10}$ or more are preferred.

Antibodies specific for the C-type lectins of the present invention are useful, for example, as probes for screening DNA expression libraries and/or for detecting the presence of members of the C-type lectin group of the present invention in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include, but are not limited to, U.S. Pat. Nos. 3,817,837; 3,850,752; 3,939,350; 3,996,345; 4,277,437; 4,275,149; and 4,366,241.

The novel calcium-dependent lectins of the present invention, as specifically exemplified by XL35, HL-3 and HL-35, are useful for "decorating" their respective targets in animal tissue or cell samples, especially from vertebrates. XL-35 is stored in oocyte cortical granules and it specifically binds to melibiose-like moieties. HL-3 and HL-13 are stored in cells and tissues of endothelial origin, although not all cells and tissues of endothelial origin. HL-3 and HL-13 do not appear to bind specifically to melibiose. These lectin family members are especially useful in binding experiments when coupled to a substance which gives a detectable signal (radionuclides, fluorescent or chemiluminescent molecules and the like). Alternatively, a labeled antibody specific for the lectin can be used to visualize sites where the lectin has bound. Similarly if the lectin is covalently bound to a compound such as biotin, a second molecule such as avidin or streptavidin can mediate further binding with concomitant or secondary signals provided. It is understood in the art how to covalently join signal generators to proteins, with the proviso that the lectin-target site binding is not disrupted.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein. All references cited in the present application are incorporated by reference herein.

The following examples are provided for illustrative purposes, and are not intended to limit the scope of the invention as claimed herein. Any variations in the exemplified articles and/or methods which occur to the skilled artisan are intended to fall within the scope of the present invention.

EXAMPLES

Example 1

Materials

Restriction enzymes, *Thermus aquaticus* DNA polymerase, agarose, and other chemicals were obtained from commercial sources. Nitrocellulose filters, DNA labeling kits, [γ-32P] dCTP, [S$^{35}$]-methionine and Amplify reagent were purchased from Amersham, Arlington Heights, Ill. Nick and Nap-5 desalting columns were purchased from Pharmacia, Piscataway, N.J. Ultrafree-MC Low Binding Durapore Membranes were purchased from Millipore, Bedford, Mass., and used for gel purification of DNA fragments. Ready polyacrylamide gel and Zeta-Probe GT nylon membranes for Southern analysis were purchased from Bio-Rad, Hercules, Calif. N-glycanase, protease inhibitor cocktail tablets, and PCR Master were from Boehringer, Indianapolis, Ind. BSA, IPTG, melibiose and immobilized melibiose were from Sigma Chemical Company, St. Louis, Mo. Sephaglas reagents were from Pharmacia, Piscataway, N.J. Ni$^{++}$-NTA columns and vectors used to construct the 6-His tag were from Qiagen, Chatsworth, Calif., and were used according to the manufacturer's instructions. The TA cloning system was from Invitrogen, San Diego, Calif. Oligonucleotides were prepared by automated synthesis using commercially available equipment. The BCA protein assay kit was from Pierce Chemical Co., Rockford, Ill. The SVEC cell line (mouse lymph node endothelial cell transformed by the SV40 virus) was originally obtained from the American Type Culture Collection, Rockville, Md. Fetal calf serum was obtained from Upstate Biotechnology Inc. The human small intestine 5'-Stretch cDNA library, λgt10 cDNA insert screening amplimer set, and human multiple tissue northern (MTN) blots were obtained from Clontech, Palo Alto, Calif. The TNT T7 coupled reticulocyte lysate system (in vitro translation kit), canine pancreatic microsomal membranes, and RNAsin ribonuclease inhibitor were from Promega, Madison, Wis. Somatic Cell Hybrid PCRable DNAs for chromosomal localization were products of BIOS Laboratories, Inc.

Example 2

Lectin Purification and Generation of PCR Primers

The oocyte lectins were purified using a procedure previously described (Roberson and Barondes, 1982, supra), followed by a C$_4$-reverse phase HPLC step using acetonitrile-TFA buffers to desalt and concentrate the lectins. An aliquot of the protein peak from the column was dried, reduced with dithiothreitol, alkylated with iodoacetamide, resuspended in urea, and subjected to exhaustive tryptic digestion. The digested sample was chromatographed on a reverse phase HPLC column, and two of the resolved peaks were subjected to gas phase Edman degradation. The isolated peptides yielded the following sequences: Peak 43-ESCNAEHVCIGGGGYFPEADPR (SEQ ID NO:7) and Peak 54-SQFTPGYIQFRPINTEK (SEQ ID NO:8). Two degenerate oligonucleotides were designed based on the peptide sequences: Peak 54 primer: CARTTYACICCIGGI-TAYATHCARTT (SEQ ID NO:9), Peak 43 PRIMER: CIC-CDATRCAIACRTGYTCIGCRTTRCA (SEQ ID NO:10). Nucleotides are abbreviated according to IUPAC convention.

Example 3

Digestion by N-glycanase

Lyophilized affinity-purified oocyte lectin (6 mg) was brought to 100 μl with a solution of 0.1 M β-mercaptoethanol/0.1% SDS. The sample was heated at 100 for 30 min, after which 25 μl of 0.5 M Tris-HCl, pH 7.5, was added, followed by 10 μl of 0.1 M phenanthroline, 10 μl of 10% Triton X-100, and 3 μl of N-glycanase (200 U/ml). The sample was then incubated for 18 hr at 35° C., after which an additional 3 ml of enzyme was added and the incubation continued for 4 hr. The protein was then precipitated by addition of trichloroacetic acid and resuspended in reducing sample buffer for SDS-PAGE. The control incubation was handled exactly as described, except no enzyme was added. SDS-PAGE was performed using gradient 4–15% polyacrylamide gels (Bio-Rad), which were stained with Coomassie blue.

Example 4

Analysis of Multimer Form of XL-35

XL-35 is localized in oocyte cortical granules as a multimer of about 500 kDa. To analyze the properties of oligomerized XL-35, purified XL-35 was disrupted by heating at 100° C. for 10 min under non-reducing conditions (2% SDS, 50 mM Tris-HCl, 15% glycerol, and 0.02% bromophenol blue) or reducing conditions (100 mM β-mercaptoethanol added) and was separated by electrophoresis through gradient 4–15% acrylamide slab gels. After electrophoresis, XL-35 was visualized by staining with Coomassie blue or by immunoblotting using anti-XL35 antibody and alkaline phosphatase conjugated anti-rabbit IgG as the secondary antibody.

Example 5

Erythrocyte Agglutination Assay

The assay was performed essentially as described using trypsinized, glutaraldehyde-fixed rabbit erythrocytes

[Barondes and Roberson (1987) *Methods Enzymol.* 138, 516–20] in TCS buffer (10 mM Tris, pH 7.6, 10 mM CaCl$_2$, 150 mM NaCl). To compare the agglutination properties of both the purified and recombinant lectins, the two lectins were assayed under similar conditions. Because the eluted recombinant lectin was in 8 M urea, a solution of purified non-recombinant lectin was also brought to 8 M with a concentrated urea solution. The agglutination assay was performed using 10 mg of either recombinant or native XL35 lectin in 25 ml TCS and 8 M urea was added to wells of a 96-well microtiter plate. Next, 25 ml of TCS alone or TCS containing 0.4 M EDTA or 1.0 M melibiose or 1.0 M sucrose was added to the wells and mixed with the lectin solution. To this solution, 50 ml of a 1:1 suspension of trypsinized, glutaraldehyde-fixed rabbit erythrocytes in TCS was added and the contents of the wells were mixed by trituration. The final concentration of urea in the wells was 2 M, while that of EDTA was 0.10 M and that of melibiose and sucrose were 0.25 M. Agglutination activity was scored after 1.5 hr. at room temperature using an inverted microscope on low power. After 1.5 hr in TCS plus 2 M urea, the purified oocyte lectin retained about 25–50% of the agglutination activity observed when it was assayed in TCS alone, but the relative abilities of various sugars to inhibit the agglutination reaction were similar in the presence or absence of urea. The recombinant lectin precipitated in the absence of urea; therefore, at least 2 M urea was used in the agglutination assay.

Example 6
Generation of a PCR Product and cDNA Library Screening

Total RNA from *Xenopus laevis* ovary was isolated by the guanidinium isothiocyanate method [Chirgwin et al. (1979) *Biochemistry* 18, 5294–5299], and 15 μg was subjected to reverse transcription using MMLV reverse transcriptase and oligo-d(T) primers as described in the Perkin Elmer RT-PCR kit. The cDNA preparation was subjected directly to PCR using 3 μM of each degenerate primer. The thermal cycling conditions were 95° C., 1 min; 55° C., 1 min; 72° C., 1 min, for a total of 30 cycles. The amplification products were resolved on a 3% agarose gel, and a 159 pb PCR amplification product was purified and subcloned into the pCR II vector using the TA Cloning kit (Invitrogen, San Diego, Calif.). A *Xenopus laevis* ovary cDNA library in λgt11 [Rebagliati et al. (1985) *Cell* 42, 769–777] was screened by plaque hybridization using the cloned 159 pb PCR product as a radiolabeled probe. The 159 pb amplimer was excised from pCR II by digestion with EcoRI and isolated using Sephaglas reagents (Pharmacia, Piscataway, N.J.). Twenty nanograms of DNA were labeled using [gamma-$^{32}$P] dCTP and the Mega-Prime labeling kit (Amersham, Arlington Heights, Ill.). Unincorporated nucleotides were removed by desalting over a Sepharose G-50 gel filtration column (nick column, Pharmacia). Filter lifts were prepared using nylon membrane (HyBond, Amersham) and UV crosslinked using a Stratalinker (Stratagene, La Jolla, Calif.). Prehybridization was carried out at 42° C. in 50% formamide, 1×Denhardts, 5×SSC, 0.1% SDS and 100 ng/ml heat-denatured herring sperm DNA. Hybridization was performed in the same solution with the addition of heat-denatured radiolabeled probe to a final concentration of 1×10$^6$ cpm/ml. Positive phage clones identified by plaque hybridization were purified through four rounds of plaque purification. Lambda DNA from positive clones was isolated from 100 ml LB cultures containing 10 mM MgSO$_4$ and 0.2% maltose using *Escherichia coli* Y1090 host cells and the polyethylene glycol precipitation procedure followed by chromatography over a Qiagen Tip-100 column as described by the manufacturer (Qiagen, Chatsworth, Calif.). The insert from one of the phage clones was excised by digestion with EcoRI, resolved on a 1% agarose gel, subcloned into pBluescript SK- (Stratagene) and sequenced. This product represented a 401 pb partial clone due to an internal EcoRI restriction site and was used as a hybridization probe for Southern and Northern analyses. The full length insert from one of the lambda clones was isolated by PCR amplification using purified lambda DNA as a template, and λgt11 forward and reverse primers (New England BioLabs, Beverly, Mass.) and Taq polymerase. The ~1.2 kb amplification product was subcloned into the pCR II vector, and the ends were sequenced. Exact match primers were then designed against the 5' and 3' untranslated regions of the lectin cDNA sequence (5' primer: GGAACTTGGTACTAAGCTCCAT-GAAAG (SEQ ID NO:11); 3' primer: ATCTCAAGACAG-GATTGTGGTTTAATAAAG; SEQ ID NO:12) and used to amplify the coding regions from the remaining clones using the purified λgt11 DNA preparations as templates. The resulting amplimers were subcloned into pCR II and fully sequenced.

Example 7
Expression of Lectin cDNA and Purification of Recombinant Protein

The predicted signal peptide cleavage site was determined to be between amino acids 18 and 19 (Table 1) [von Heinje, G. (1985) *J. Mol. Biol.* 184, 99–105]. PCR primers were designed to amplify the coding sequence excluding the signal peptide sequence (amino acids 19–313). Two restriction enzyme cleavage sites, SalI and PstI, were designed into the 5' and 3' primers, respectively: 5' primer: CCCGTC-GACGAACCTGTTGTAATAGTAGCCTCAA AA, SEQ ID NO:13; 3'primer: CCCCTGCAGTCATA-GATAGAAAAGTAATACAGCGG CCTC, SEQ ID NO:14. The amplimer obtained using these primers and the XL35 cDNA clone as a template was cloned directly into the QIAexpress Vector (pQE-9) (Qiagen) using SalI-PstI restriction sites. This procedure appended the sequence, MRGS(His)6GS, to the N-terminus. The resulting plasmid was transfected into *E. coli* host strain SB13009 (pREP4). Recombinant protein production was induced with 1 mM IPTG. The purification of recombinant protein was performed according to the instructions provided by the supplier. Briefly, the cells were harvested and subjected to one freeze-thaw, after which 10 g of the pellet (wet weight) were resuspended in 50 ml of 6 M guanidine hydrochloride, 0.1 M NaH$_2$PO$_4$, 0.01 M Tris, pH 8.0. After stirring for 1 hr, the solution was centrifuged (10,000×g, 20 min, 4° C.) and the clear supernatant loaded on a 4 ml Ni-NTA chromatography column which was equilibrated and eluted using the manufacturer's instructions. The majority of the major protein band that migrated at 35 kDa on SDS-PAGE bound to the column. After washing the column with 8 M urea, 0.1 M NaH$_2$PO$_4$, 0.01 M Tris, pH 8.0, the column was step-eluted with the same buffer at pH 6.3, and then pH 5.9, and finally the 35 kDa protein band was eluted using the same buffer at pH 4.5. The yield of purified recombinant protein was about 250 mg/liter of culture after purification on the nickel column.

Example 8
Human Homologs of XL-35

XL-35 cDNA and peptide sequences were used to search protein and DNA sequence databases, and a single entry was identified from non-Xenopus sources. The sole sequence match was a fragmentary 251 bp cDNA sequence obtained from a human heart cDNA library (GenBank, Accession number Z36760) as an expressed sequence tag (EST) (Table 2). Using the human EST sequence, we designed oligonucleotide primers (underlined sequences of Table 2): 5' primer: CAGACCTTCTGTGACATGACCTCT, SEQ ID NO:15; 3' primer: AAGATGCCCAGGTCCTTGGCCTGG, SEQ ID NO:16. The human placenta, spleen, and liver cDNAs were subjected directly to PCR reactions in a 25 μl reaction volume containing 1 μM of each primers, 10 ng of each cDNA, 0.2 mM of each dNTP, 10 mM Tris-HCl, 50 mM KCl, 1.5 mM MgCl₂, and 1.5 units of Taq polymerase. The thermal cycling conditions were: 92° C., 1 min; 55° C., 1 min; 72° C., 1 min, for a total of 35 cycles. The amplification products were separated on a 0.7% agarose gel and purified using Sephaglas™ BandPrep kit (Pharmacia, Piscataway, N.J.). Each amplimer was subcloned into the pCR II vector using the TA Cloning kit (Invitrogen, San Diego, Calif.) and fully sequenced. The deduced peptide sequences from the PCR products, the human heart EST sequences, and the XL-35 cDNA clone were aligned to compare their sequence identities. The amplimers were obtained from human liver, spleen, and placenta cDNA sources that were essentially identical to the human heart cDNA sequence in the database.

The amplification products (251 bp) obtained from the PCR reaction with human liver cDNA and the primers designed as above were resolved on a 1.0% agarose gel and purified. The human small intestine 5'-Stretch λgt10 cDNA library (Clontech, Palo Alto, Calif.) was screened by plaque hybridization using the 251 bp PCR product as a radiolabeled probe. Eighty nanograms of DNA were labeled using [γ-$^{32}$P] dCTP and the Mega-Prime labeling kit (Amersham). Unincorporated nucleotides were removed by desalting over a Sepharose G-50 column (Nick column, Pharmacia). Filter lifts were prepared using nylon membranes (HyBond, Amersham) and UV crosslinked using a Stratalinker (Stratagene, La Jolla, Calif.). Pre-hybridization was carried out at 42° C. in 50% formamide, 1×Denhardts, 5×SSC, 0.1% SDS and 100 ng/ml heat-denatured herring sperm DNA. Hybridization was performed in the same solution with the addition of heat-denatured radiolabeled probe to a final concentration of $1.2 \times 10^6$ cpm/ml. Positive phage clones identified by plaque hybridization were purified through four rounds of plaque purification. Positive lambda clones were each propagated using E. coli Y1090 host cells in 100 ml LB containing 10 mM MgSO₄ and 0.2% maltose cultures containing the Y1090 host cell. The polyethylene glycol precipitation procedure was used to precipitate phage, followed by chromatography over a Qiagen Tip-100 column as described by the manufacturer (Qiagen, Chatsworth, Calif.). The full length insert from the lambda clones was isolated by PCR amplification using the λgt10 cDNA insert screening amplimer set and purified lambda DNA as a template. From this screening procedure, a total of 13 different sizes (0.7~2.4 kb) of cDNA clones were isolated. Seven cDNA clones (greater than 1.2 kb) were subcloned into the pCR II vector and fully sequenced. The sequencing results showed that 6 clones (named as HL-13) had same nucleotide sequence but one clone (named as HL-3) had a different sequence (Tables 3, 4).

All cDNA clones and genomic clones were sequenced by using Taq polymerase in the dideoxy dye-terminator reaction using T7, SP6 polymerase primers, and synthetic primers. The sequencing results were analyzed on an Applied Biosystems 373A automated DNA sequencer. DNA sequence data were assembled into a contiguous sequence data base as described in Staden, R. (1987) *Nucleic Acid and Protein Sequence Analysis: A Practical Approach*. (Bishop and Rawlings, Eds.), IRL Press Ltd., Oxford. A sequence similarity search between protein or DNA sequences was performed using the Bestfit, Pileup, Fasta, and Tblast programs of the University of Wisconsin Genetics Computer Group (GCG software, version 8.0).

Example 9

Expression of Human Homolog cDNAs

In procedures similar to those for the bacterial expression of XL-35, the predicted signal peptide cleavage sites of HL-3 and HL-13 were determined, and PCR primers were designed to amplify the coding sequences excluding the signal peptide sequence (Tables 3, 4). Two restriction enzyme cleavage sites, SalI and HindIII, were designed into the 5' and 3' primers for HL-3 and HL-13 cDNA, respectively (Tables 3, 4). 5' primer: CCCGTCGACTGGAGTACAGATGAGGCTAATACTTAC. SEQ ID NO:17; 3' primer: CCCAAGCTTTCAACGATAGAATAGAAGCACAGCT GC, SEQ ID NO:18; for HL-3 and 5' primer: CCCGTCGACTCTTCTCTTGAGATGCTCTCGAGGGAA, SEQ ID NO:19; 3' primer: CCCAAGCTTTCATCTATAGAACAAGAGTACAGGCGC, SEQ ID NO:20, for HL-13. The amplimers obtained using these primers and HL-3 and 13 cDNA clones as templates were subcloned and expressed with MRGS(His)6 added to the N-terminus, using same method as described for XL35. The induction, purification and agglutination assay were carried out by the same methods used for XL-35 expression. Finally, purified fractions showed the 34~35 kDa protein bands on SDS-polyacrylamide gel electrophoresis. These fractions were subjected to erythrocyte agglutination and injected into rabbits to produce antisera.

Example 10

Preparation of Antisera to Native XL35, Recombinant XL-35 and Recombinant HL-13

Purified XL35 and HL-13 proteins (each 0.3 mg) from recombinant E. coli and purified native *Xenopus laevis* oocyte lectin (0.1 mg) were separately emulsified in an equal volume of Freund's complete adjuvant and injected into a male New Zealand white rabbit. Recombinant XL35 and HL-13 was in 8 M urea solution and directly used without dialysis to remove urea. At 20-day intervals, additional booster immunizations were given with 0.3 mg of protein and Freund's incomplete adjuvant. Western blots were performed using the native form of XL-35 or bacterial expressed XL-35, HL-3, and HL-13 (FIG. 4).

Example 11

Isolation of Genomic DNA Clones

Genomic clones were isolated as inserts in P1 vectors by a PCR screening approach. First, two primer pairs for each HL-3 and HL-13 cDNA clones was designed. These primer pairs have relatively low sequence homology to other regions of HL-3 and HL-13 cDNA clones (Boxed sequences in Tables 3, 4). The primer sequences are: 5' primer: ATACTTTCCAGAGGCCAGTCCCCAG, SEQ ID NO:21, 3' primer: AGGTCTGGGTTCCCTCCCACAAAAC, SEQ ID NO:22, for HL-3 and 5' primer: GTTCTTCCCACAGGGCAAACCCCGT, SEQ ID NO:23, 3' primer: TCTGCCCTGACACCGGAGAGCTCTG, SEQ ID NO:24, for HL-13. The PCR reactions were performed in a 25 μl reaction volume containing 1 μM of each primers, 50 ng of human genomic DNA, 0.2 mM each dNTP, 10 mM Tris-HCl, 50 mM KCl, 1.5 mM MgCl₂, and 1.5 units of Taq polymerase. The thermal cycling conditions were: 94° C., 1 min; 65° C., 1 min; 72° C., 1 min, for a total of 35 cycles. Around 160 bp of amplimers were obtained from PCR reactions (dotted-line sequences in Tables 3, 4). The sequence of each amplimer was the same as that of each cDNA clone, which implied that these regions do not have any introns. These primers and PCR reaction conditions were used for the screening of genomic DNA clones. This screening yielded two genomic clones for both of HL-3 and HL-13. These genomic clones were partially sequenced using synthetic primers that were designed for the sequencing of cDNA clones to compare their genomic organization. One genomic clone from HL-3 and HL-13 was used for Fluorescent in situ Hybridization (FISH) analysis.

Example 12
Chromosomal Localization and FISH Analysis

Somatic cell hybrid DNAs (BIOSMAP Laboratories, Inc.) were screened for the HL-3 and HL-13 gene by PCR. The DNAs from two human hybrid panels of human/rodent cells were screened by PCR with the primers which were used for genomic DNA screening. PCR was performed using the same conditions as those described for the isolation of genomic clones. The first hybrid panel consisted of 24 human/rodent hybrid cell lines, each containing a single human chromosome. Rodent and human genomic DNAs were also tested as both a negative and positive control. Amplified fragments were obtained from the human genomic DNA controls but not from hamster or mouse chromosome DNA, demonstrating species specificity of the primer pairs. The second hybrid panel consisted of 20 human/mouse hybrid cell lines, each carrying one or more specific human chromosomes.

Fluorescent in situ Hybridization (FISH) analysis was carried out by Genomic Systems, Inc. Purified DNAs from each genomic clone were labeled with digoxigenin dUTP by nick translation. Labeled probes were combined with sheared human DNA and hybridized to normal metaphase chromosomes derived from PHA-stimulated peripheral blood lymphocytes in a solution containing 50% formamide, 10% dextran sulfate and 2×SSC. Specific hybridization signals were detected by incubating the hybridized slides in fluoresceinated anti-digoxigenin antibodies, followed by counterstaining with DAPI. The initial experiments resulted in specific labeling of the long arm of the group A chromosome in the case of both HL-3 and HL-13. A second experiment conducted in which were concluded an anonymous probe previously mapped to 1p34 and confirmed by cohybridization, a centromere specific probe, and each genomic DNA probe. The locations of the HL-3 and HL-13 genes were determined by measurements of each 10 specifically hybridized samples.

Example 13
Northern Blot Analysis

The initial Northern blot analysis was performed before screening full length of human homolog cDNA clones. The 100 ng of purified amplimer (251 bp) was obtained from PCR with human liver cDNA and primers that were designed based upon human heart EST sequence. This amplimer was labeled using [γ-$^{32}$P] dCTP and the Mega-Prime labeling kit (Amersham) according to manufacturer's instructions. This radiolabeled DNA fragment was used to probe Northern blots of various human tissue RNAs (human multiple tissue northern (MTN) blot, Clontech, Palo Alto, Calif.). All blots were probed using the same protocol in which the prehybridization buffer consisted of 75 ml of 1 M phosphate buffer pH 7.0, 0.3 ml of 0.5 M EDTA pH 8.0, 52.5 ml of 20% SDS 1.5 g of fatty acid free BSA, 1.5 ml of a 10 mg/ml denatured herring sperm DNA, and 20.7 ml of water. The hybridization buffer was identical, except for the addition of denatured radiolabeled probe. Prehybridization was performed for 2 hours at 65° C. and hybridization was performed overnight at 65° C. The blots were washed three times at 65° C. for 15 minutes in 50 ml of 40 mM phosphate buffer pH 7.0, 1% SDS, 1 mM EDTA and 0.5% fraction V BSA and an additional three times at 65° C. for 15 minutes in the same buffer excluding BSA. The blots were then washed in 50 ml of 1 M phosphate buffer pH 7.0 at room temperature for 10 minutes and data collected using a Molecular Dynamics phosphoimager or autoradiography.

After sequencing the full length of two different human homolog cDNA clones, we obtained specific probes for each HL-3 and HL-13 cDNA clone using PCR as described above (dotted-line sequences in FIGS. 4, 5). The two 161 bp amplimers obtained from PCR had 58/161 mismatches. These two amplimers were used to probe the MTN blot using the same method as described above (FIG. 10).

Example 14
In Vitro Translation

Two restriction enzyme cleavage sites, ApaI and PstI, were designed into the 5' and 3' primers for XL35 cDNA clones, respectively:

5' primer: GGGCCCTGAAAGATGCTGGTGCACAT-TCTTCTCC
TG, SEQ ID NO:25,

3' primer: CCCCTGCAGTCATAGATAGAAAAG-TAATACAGC
GGCCTC, SEQ ID NO:26.

Similarly, two restriction enzyme cleavage sites, ApaI and SpeI, were designed into the 5' and 3' primers for HL-3 and HL-13 cDNA clones, respectively:

5' primer: GGGCCCGACTCAGACAAGATTACAAT-GAACCA
ACTC, SEQ ID NO:27,

3' primer: ACTAGTAGGTCTGGGTTCCCTCCCA-CAAAACT
CTCA, SEQ ID NO:28, and 5' primer: GGGCCCTCTGTAAGGATGCTGTC-CATGCTGAG
GACA, SEQ ID NO:29, 3' primer: ACTAGTCTCGCCCTGACACCG-GAGAGCTCTG
TCTCA, SEQ ID NO:30.

The amplimers obtained using these primers and the XL35, HL-3 and HL-13 cDNA clones, containing the entire open reading frames as a template, were cloned directly into pBluescript II using ApaI-PstI and ApaI and SpeI restriction sites. These clones were transcribed and translated in vitro using the T7 polymerase promoter of pBluescript II and an in vitro translation kit (TNT T7 Coupled Reticulocyte Lysate Systems, Promega, Madison, Wis.). Protein synthesis was carried out for 1.5 hr at 37° C. in a 50 µl reaction volume containing 25 µl of rabbit reticulocyte lysate, 2 µl of TNT reaction buffer, 1 µl of T7 polymerase (1 U), 1 µl of amino acid mixture minus methionine (1 mM), 4 µl of [$^{35}$S]-methionine (1,000 Ci/mmol, 10 mCi/ml), 1 µl of Rnasin Ribonuclease Inhibitor (40 U/µl), and 5 µg of each DNA templates. Incubations containing microsomal membranes were performed by addition of 5 µl of canine microsomal membranes (Promega) per 50 µl reaction before the translation reaction was initiated. Positive and negative control reactions contained luciferase control DNA and a plasmid without insert. Samples were then denatured directly in SDS sample buffer or processed proteolysis by trypsin. The proteolysis reactions were performed by addition of trypsin (Sigma) to 100 μg/ml, with or without 0.1% Triton X-100, followed by incubation at 0° C. for 1 hr. Proteolysis was terminated by addition of trypsin inhibitor (Sigma) to 200 μg/ml and boiling in SDS sample buffer. Aliquots were subjected to 4–15% SDS-PAGE and the results were analyzed by autoradiography (FIG. 9).

Example 15
Immunoblot Experiments

Expression of other vertebrate lectin homologs was determined by immunoblotting of mouse, rat, *Xenopus laevis* heart, and SVEC cell line extracts (mouse lymph node endothelial cell). Briefly, 5 g of each mouse and *Xenopus laevis* heart (Pel-freeze, Rogers, AR) was dissolved in 20 ml of TCS containing 8 M urea. The tissues were homogenized by grinding with mortar and pestle. The homogenized samples were clarified by centrifugation at 100,000×g for 30 min at 4° C. The protein concentrations of supernatants were determined, and aliquots were subjected to 4–15% SDS-PAGE. Rat heart extract was prepared using a procedure previously described (333). Briefly, five grams of rat heart was homogenized in 10 volumes of cold acetone using a homogenizer and filtered on Whatman paper. After drying the acetone powder, it was re-homogenized by TCS and centrifuged at a 100,000×g for 1 hr at 4° C. The supernatant was then subjected to SDS-PAGE and immunoblotting. SVEC cells were lysed with a 2% Triton X-100 containing lysis buffer (50 mM MES, pH 6.5, 150 mM NaCl, 25% glycerol) and sonicated on ice for 15 min. After microcentrifugation, the supernatant was separated by 4–15% SDS-PAGE. Immunoblotting was performed with the rabbit polyclonal antibody against native XL-35 or recombinant human lectin. Bound primary antibody was visualized with alkaline phosphatase conjugated rabbit IgG.

Example 16
Melibiose Affinity Chromatography

The rabbit, mouse, *Xenopus laevis* heart extracts, and various in vitro translation products were applied to a column of immobilized melibiose-agarose to analyze carbohydrate binding specificity. The heart extracts of rabbit, mouse, and *Xenopus laevis* were prepared by the method as described above and applied to a melibiose affinity column (total volume, 1 ml on Econo column) that was pre-equilibrated with TCS. After washing with 10 ml of TCS containing 0.3 M sucrose, bound protein was eluted with TCS containing 0.1 M EDTA. One ml of each fraction was collected and subjected to western blotting followed by 4–15% SDS-PAGE. Each 30 μl of in vitro translation product was diluted with 2×TCS (1:1) and applied to the melibiose column using same method. After separation of fractions on 4–15% SDS-PAGE, the results were analyzed by autoradiography.

Example 17
Immunofluorescence Microscopy

SVEC cells grown on coverslips were rinsed twice with PBS and fixed with 2% neutral buffered formalin (Fisher Scientific, Pittsburgh, Pa.) in Hank's balanced salt solution (HBSS, Sigma) for 10 min at 37° C. After washing with PBS, some of the cells were permeabilized with 2% saponin in PBS containing 10% BSA for 10 min at 37° C. Non-permeabilized cells (as a control) were prepared by incubation without saponin. The cells were then incubated with primary antisera (1:1,000) or control mouse pre-immune serum (1:1,000). After rinsing off the primary antisera with excess PBS at least three times, the cells were incubated next with FITC-coupled goat anti-rabbit IgG Ab. The cover slips were rinsed again with PBS and mounted in PerFluor Aqueous Mountant (Lipshaw Immunon). Immunoreactivity was visualized and photographed with a Laser Scanning Confocal Microscope (Bio-Rad, MRC 600).

Example 18
Immunohistochemistry

Human colon, heart, thymus, and ovary tissue sections were incubated with the anti-native XL antisera or anti-recombinant HL-13 antisera and visualized by horseradish peroxidase conjugated goat anti-rabbit IgG, with AEC as the color substrate. The slides are counterstained with hematoxylin.

TABLE 1

Nucleotide and Deduced Amino Acid Sequences for *Xenopus laevis* lectin XL-35 cDNA.
See also SEQ ID NO:2 and SEQ ID NO:3.

```
-32                                                    GGCTTGGAACTTGGTACTAAGCTCCATGAAAG

1 ATGCTGGTGCACATTCTTCTCCTGCTGGTGACTGGTGGGCTCTCTCAGTCTTGTGACCCTGTTGTAATAGTAGCCTCAAAAAACATGGTG
  1 H  L  V  H  X  L  L  L  L  V  T  G  G  L  S  Q  S  C  D  P  V  V  X  V  A  S  K  N  M  V

91 AAGCAGCTGGATTGTGATAAATTCAGAAACTGCAAGGAGATCAAAGATTCAAACGAAGAAGCACAAGATGGAATATACACACTGACCTCT
 31 K  Q  L  D  C  D  K  F  R  N  C  K  E  Y  K  D  S  N  E  E  A  Q  D  G  I  Y  T  L  T  S

181 CCAGATGGGATATCCTACCAGACCTTCTGTGACATGACTACAAATGGAGGAGGATGGACTTTGGTGGCGAGTGTTCATGAGAACAACATG
 61 P  D  G  Y  S  Y  Q  T  F  C  D  M  T  T  N  G  G  W  T  L  V  A  S  V  H  E  N  N  M

271 GCAGGGAAGTGCACTATAGGGGATCGCTGGTCCAGCCAACAGGGGAATCGAGCTGACTATCCAGAGGGCGATGGCAACTGGGCAAACTAT
 91 A  G  K  C  T  I  G  D  R  H  S  S  Q  Q  G  N  R  A  D  Y  P  E  G  D  G  N  W  A  N  Y

361 AATACATTTGGATCAGCTGGTGGCGCAACTAGTGATGACTACAAGAATCCTGGCTATTATGATATTGAAGCATATAACCTTGGGGTGTGG
121 N  T  F  G  S  A  G  G  A  T  S  D  D  Y  K  N  P  G  Y  Y  D  I  E  A  Y  N  L  G  V  W

451 CACGTGCCCAACAAGACTCCCCTGAGTGTTTGGAGGAATTCATCGCTACAGAGATACCGTACAACAGATGGCATCCTTTTCAAACATGGA
151 H  V  P  N  K  T  P  L  S  V  W  R  N  S  S  L  Q  R  Y  R  T  T  D  G  I  L  F  K  H  G
                *                         *

541 GGAAACCTCTTCAGTCTGTATCGGATCTATCCAGTGAAATATGGTATAGGAAGCTGCTCAAAGGACAGTGGCCCAACTGTGCCAGTAGTG
181 G  N  L  F  S  L  Y  R  I  Y  P  V  K  Y  G  I  G  S  C  S  K  D  S  G  P  T  V  P  V  V
```

TABLE 1-continued

Nucleotide and Deduced Amino Acid Sequences for *Xenopus laevis* lectin XL-35 cDNA.
See also SEQ ID NO:2 and SEQ ID NO:3.

```
631 TACGATCTTGGAAGTGCTAATTTAACAGCTTCTTTCTACTCTCCAGGTTTCAGAAGTCAGTTTACCCCTGGCTATATCCAATTTCGGCCA
                                                                    ...........................
211 Y  D  L  G  S  A  N  L  T  A  S  F  Y  S  P  G  F  R  S  Q  F  T  P  G  Y  I  Q  F  R  P
                      *

721 ATTAACACTGAAAAAGCTGGCTCTGGCGCTATGTCCGGGAATGAAGATGGAGCATGCAATGTGGAACATGTGTGCATAGGAGGAGGTGGC
                                                                    ...........................
241 I  N  T  E  K  A  A  L  A  L  C  P  G  M  K  M  E  S  C  N  V  E  H  V  C  I  G  G  G

811 TACTTTCCAGAAGCAGACCCTCGGCAATGTGGAGACTTTGCAGCCTATGACTTTAATGGATATGGAACCAAAAAGTTTAACAGTGCGGGC
271 Y  F  P  E  A  D  P  R  Q  C  G  D  F  A  A  Y  D  F  N  G  Y  G  T  K  K  F  N  S  A  G

901 ATAGAGATAACTGAGGCCGCTGTATTACTTTTCTATCTATGATCTGAAATCTTACTAAAAATAACTAGTACAAAAACAAGAATAGTAAGT
301 I  E  I  T  E  A  A  V  L  L  F  Y  L

991 GCATTGTTTGGCAACTTTATTAAACCACAATCCTGTCTTGAGATAAGCCGAATTCCAGCACACTGGCG
```

Underlining indicates the portion of the cDNA used as a hybridization probe in Northern and Southern blots. Dotted underlines indicate positions of PCR primers corresponding to those designed from lectin partial peptide sequence. Asterisks denote possible glycosylation sites.

TABLE 2A

Results of TBLAST Sequence Search Using XL-35 Partial Amino Acid Sequence and Related Human Deduced Amino Acid Sequence.

```
>GB_EST4:HHEA56z z36760 H. sapiens partial cDMA sequence; clone HEA56Z; single
   read. 8/94

Length = 251

Plus Strand HSPs:
   Score = 408 (189.1 bits), Expect = 3.2e-50, P = .2e-50
   Identities = 69/83 (83%), Positives = 78/83 (93%), Frame = +1

XL-35:     67 QTFCDMTTNGGGWTLVASVHENNMAGKCTIGDRWWSSQQGNRADYPEGDGNWANYNTFGSA 126
              QTFCDMT+ GGGWTLVASVHEN+M GKCT+GDRWWSSQQG++ADYPEGDGNWANYNTFGS+

Sbjct:      1 QTFCDMTSGGGGWTLVASVHENDMRGKCTVGDRWWSSQQGSKADYPEGDGNWANYNTFGSS 180

Query:    127 GGATSDDYKNPGYYDIEAYNLGV 149
                ATSDDYKNPGYYDI+A +LG+

Sbjct:    181 EAATSDDYKNPGYYDIQAKDLGI 249
```

The subject sequence corresponds to amino acids 51–131 of SEQ ID NO:2 and the query sequence to amino acids 61–143 of SEQ ID NO:6.

TABLE 2B

Human Heart EST Nucleotide Sequence. This sequence corresponds to nucleotides 268–317 of SEQ ID NO:5.

```
  1 CAGACCTTCT GTGACATGAC CTCTGGGGGT GGCGGCTGGA CCCTGGTGGC

51 CAGCGTGCAT GAGAATGACA TGCGTGGGAA GTGCACGGTG GGCGATCGCT

101 GGTCCAGTCA GCAGGGTAGC AAAGCAGACT ACCCAGAGGG GGACGGCAAC

151 TGGGCCAACT ACAACACCTT TGGATCTTCA GAGGCGGCCA CGAGCGATGA

201 CTACAAGAAC CCTGGTTACT ACGACATCCA GGCCAAGGAC CTGGGCATCT

251 T
```

TABLE 3

Nucleotide and Deduced Amino Acid Sequence of Human HL-3 from cDNA.
HL-3

```
-106                                                                                      TTGGAGAAAGCTGCAC

-90  TCTGTTGAGCTCCAGGGCGCAGTGGAGGGAGGGAGTGAAGGAGCTCTCTGTACCCAAGGAAAGTGCAGCTGAGACTCAGACAAGATTACA

1  ATGAACCAACTCAGCTTCCTGCTGTTTCTCATAGCGACCACCAGAGGATGGAGTACAGATGAGGCTAATACTTACTTCAAGGAATGGACC
   1  M  N  Q  L  S  F  L  L  F  L  I  A  T  T  R  G  W  S  T  D  E  A  N  T  Y  F  K  E  W  T

91  TGTTCTTCGTCTCCATCTCTGCCCAGAAGCTGCAAGGAAATCAAAGACGAATGTCCTAGTGCATTTGATGGCCTGTATTTTCTCCGCACT
  31  C  S  S  S  P  S  L  P  R  S  C  K  E  I  K  D  E  C  P  S  A  F  D  G  L  Y  F  L  R  T

181  GAGAATGGTGTTATCTACCAGACCTTCTGTGACATGACCTCTGGGGGTGGCGGCTGGACCCTGGTGGCCAGCGTGCATGAGAATGACATG
  61  E  N  G  V  I  Y  Q  T  F  C  D  M  T  S  G  G  G  W  T  L  V  A  S  V  H  E  N  D  M

271  CGTGGGAAGTGCACGGTGGGCGATCGCTGGTCCAGTCAGCAGGGCAGCAAAGCAGACTACCCAGAGGGGGACGGCAACTGGGCCAACTAC
  91  R  G  K  C  T  V  G  D  R  W  S  S  Q  Q  G  S  K  A  D  Y  P  E  G  D  G  N  W  A  N  Y

361  AACACCTTTGGATCTGCAGAGGCGGGCACGAGCGATGACTACAAGAACCCTGGCTACTACGACATCCAGGCCAAGGACCTGGGCATCTGG
 121  N  T  F  G  S  A  E  A  G  T  S  D  D  Y  K  N  P  G  Y  Y  D  I  Q  A  K  D  L  G  I  W

451  CACGTGCCCAATAAGTCCCCCATGCAGCACTGGAGAAACAGCTCCCTGCTGAGGTACCGCACGGACACTGGCTTCCTCCAGACACTGGGA
 151  H  V  P  N  K  S  P  M  Q  H  W  R  N  S  S  L  L  R  Y  R  T  D  T  G  F  L  Q  T  L  G
             *                    *

541  CATAATCTGTTTGGCATCTACCAGAAATATCCAGTGAAATATGGAGAAGGAAAGTGTTGGACTGACAACGGCCCGGTGATCCCTGTGGTC
 181  H  N  L  F  G  I  Y  Q  K  Y  P  V  K  Y  G  E  G  K  C  W  T  D  N  G  P  V  I  P  V  V

631  TATGATTTTGGCGACGCCCAGAAAACAGCATCTTATTACTCACCCTATGGCCAGCGGGAATTCACTGCGGGATTTGTTCAGTTCAGGGTA
 211  Y  D  F  G  D  A  Q  K  T  A  S  Y  Y  S  P  Y  G  Q  R  E  F  T  A  G  F  V  Q  F  R  V

721  TTTAATAACGAGAGAGCAGCCAACGCCTTGTGTGCTGGAATGAGGGTCACCGGATGTAACACTGAGCACCACTGCATTGGTGGAGGAGGA
 241  F  N  N  E  R  A  A  N  A  L  C  A  G  M  R  V  T  G  C  N  T  E  H  H  C  I  G  G  G  G

811  TACTTTCCAGAGGCCAGTCCCCAGCAGTGTGGAGATTTTTCTGGTTTTGATTGGAGTGGATATGGAACTCATGTTGGTTACAGCAGCAGC
 271  Y  F  P  E  A  S  P  Q  Q  C  G  D  F  S  G  F  D  W  S  G  Y  G  T  H  V  G  Y  S  S  S

901  CGTGAGATAACTGAGGCAGCTGTGCTTCTATTCTATCGTTGAGACTTTTGTGGGAGGGAACCCAGACCTCTCCTCCCAACCATGAGATCC
 301  R  E  I  T  E  A  A  V  L  L  F  Y  R

991  CAAGGATGGAGAACAACTTACCCAGTAGCTAGAATGTTAATGGCAG
```

N-terminal amino acid sequences are underlined; probe sequences used in Northern blots are marked with dotted underlining, and the human EST used in cDNA screening is underlined. Box sequences are those corresponding to PCR primers used in chromosome and genomic clone mapping.

TABLE 4

Nucleotide and Deduced Amino Acid Sequences for Human HL-13 cDNA.
HL-13

```
 -30                                                      GGGAACTCTCAGCTCCTGGCATCTGTAAGG

1  ATGCTGTCCATGCTGAGGACAATGACCAGACTCTGCTTCCTGTTATTCTTCTCTGTGGCCACCAGTGGGTGCAGTGCAGCAGCAGCCTCT
   1  M  L  S  M  L  R  T  M  T  R  L  C  F  L  L  F  S  V  A  T  S  G  C  S  A  A  A  A  S

91  TCTCTTGAGATGCTCTCGAGGGAATTCGAAACCTGTGCCTTCTCCTTTTCTTCCCTGCCTAGAAGCTGCAAAGAAATCAAGGAACGCTGC
  31  S  L  E  M  L  S  R  E  F  E  T  C  A  F  S  F  S  S  L  P  R  S  C  K  E  I  K  E  R  C

181  CATAGTGCAGGTGATGGCCTGTATTTTCTCCGCACCAAGAATGGTGTTGTCTACCAGACCTTCTGTGACATGACTTCTGGGGGTGGCGGC
  61  H  S  A  G  D  G  L  Y  F  L  R  T  K  N  G  V  V  Y  Q  T  F  C  D  M  T  S  G  G  G  G

271  TGGACCCTGGTGGCCAGCGTGCACGAGAATGACATGCGTGGGAAGTGCACGGTGGGTGATCGCTGGTCCAGTCAGCAGGGCAACAAAGCA
  91  W  T  L  V  A  S  V  H  E  N  D  M  R  G  K  C  T  V  G  D  R  W  S  S  Q  Q  G  N  K  A
```

TABLE 4-continued

Nucleotide and Deduced Amino Acid Sequences for Human HL-13 cDNA.
HL-13

```
361 GACTACCCAGAGGGGATGGCAACTGGGCCAACTACAACACCTTTGGATCTGCAGAGGCGGCCACGAGCGATGACTACAAGAACCCTGGC
121  D  Y  P  E  G  D  G  N  W  A  N  Y  N  T  F  G  S  A  E  A  A  T  S  D  D  Y  K  N  P  G

451 TACTACGACATCCAGGCCAAGGACCTGGGCATCTGGCATGTGCCCAACAAGTCCCCCATGCAGCATTGGAGAAACAGCGCCCTGCTGAGG
151  Y  Y  D  I  Q  A  K  D  L  G  I  W  H  V  P  N  K  S  P  M  Q  H  W  R  N  S  A  L  L  R
                                                       *

541 TACCGCACCAACACTGGCTTCCTCCAGAGACTGGGACATAATCTGTTTGGCATCTACCAGAAATACCCAGTGAAATACAGATCAGGGAAA
181  Y  R  T  N  T  G  F  L  Q  R  L  G  H  N  L  F  G  I  Y  Q  K  Y  P  V  K  Y  R  S  G  K

631 TGTTGGAATGACAATGGCCCAGCCATACCTGTGGTCTATGACTTTGGTGATGCTAAGAAGACTGCATCTTATTACTCACCGTATGGTCAA
211  C  W  N  D  N  G  P  A  I  P  V  V  Y  D  F  G  D  A  K  K  T  A  S  Y  Y  S  P  Y  G  Q

721 CGGGAATTTGTTGCAGGATTCGTTCAGTTCCGGGTGTTTAATAACGAGAGAGCAGCCAACGCCCTTTGTGCTGGGATAAAAGTTACTGGC
241  R  E  F  V  A  G  F  V  Q  F  R  V  F  N  N  E  R  A  A  N  A  L  C  A  G  I  K  V  T  G

811 TGTAACACTGAGCATCACTGCATCGGTGGAGGAGGCTTCTTCCCACAGGGCAAACCCCGTCAGTGTGGGGACTTCTCCGCCTTTGACTGG
271  C  N  T  E  H  H  C  I  G  G  G  G  F  F  P  Q  G  K  P  R  Q  C  G  D  F  S  A  F  D  W

901 GATGGATATGGAACTCACGTTAAGAGCACCTCCAGTCGGGAGATAACGGAGGCGCCTGTACTCTTGTTCTATAGATGAGACAGAGCTCTG
301  D  G  Y  G  T  H  V  K  S  T  S  S  R  E  I  T  E  A  P  V  L  L  F  Y  R

991 CGGTGTCAGGGCGAGACCCATCTTCCAACCCCGGCTATTTGGAGACGGAAAAACTGGAATTCTAACAAGGAGGAGAGGAGACTAAATCA

1081 CATCAATTTGCCCAAAAAAAAAACCG
```

The N-terminal sequence of the protein is underlined, dotted underlining marks the hybridization probe sequences using in Northern blot analysis; and the heart EST sequence used as a hybridization probe for cDNA library screening is underlined. The boxed sequences correspond to PCR primers used for chromosome localization and screening genomic DNA clones.

We claim:

1. A non-naturally occurring recombinant DNA molecule encoding a mature calcium-dependent lectin polypeptide having an amino acid sequence as set forth in SEQ ID NO:2, amino acids 1 to 295; an amino acid sequence as set forth in SEQ ID NO:4, amino acids 1 to 297; or an amino acid sequence as set forth in SEQ ID NO:6, amino acids 1 to 307.

2. The non-naturally occurring recombinant DNA molecule of claim 1 comprising a first region encoding an amino acid sequence as given in SEQ ID NO:2, amino acids 1 to 295.

3. The non-naturally occurring recombinant DNA molecule of claim 2 wherein the first region has a nucleotide sequence encoding said calcium-dependent lectin polypeptide as given in SEQ ID NO:1, nucleotides 87 to 971, exclusive of a translation termination codon.

4. The non-naturally occurring recombinant DNA molecule of claim 2 further comprising a second region encoding a signal sequence as given in SEQ ID NO:2, amino acids −18 to −1 immediately upstream of the first region encoding the amino acid sequence of SEQ ID NO:2, amino acids 1 to 295.

5. The non-naturally occurring recombinant DNA molecule of claim 2 wherein said second and said first regions together have a nucleotide sequence as given in SEQ ID NO:1, nucleotides 33 to 971, exclusive of a translation termination codon.

6. The non-naturally occurring recombinant DNA molecule of claim 5 further comprising a translation termination codon, wherein said translation termination codon is TGA, TAA or TAG and it is immediately downstream of nucleotide 971.

7. The non-naturally occurring recombinant DNA molecule of claim 1 encoding an amino acid sequence as given in SEQ ID NO:4, amino acids 1 to 297.

8. The non-naturally occurring recombinant DNA molecule of claim 7 wherein the nucleotide sequence encoding said calcium-dependent lectin polypeptide is as given in SEQ ID NO:3, nucleotides 155 to 1045, exclusive of a translation termination codon.

9. The non-naturally occurring recombinant DNA molecule of claim 7 further comprising a second region encoding a signal sequence as given in SEQ ID NO:4, amino acids −16 to −1 immediately upstream of the first region encoding the amino acid sequence of SEQ ID NO:4, amino acids 1 to 297.

10. The non-naturally occurring recombinant DNA molecule of claim 7 wherein said second and said first regions together have a nucleotide sequence as given in SEQ ID NO:3, nucleotides 107 to 1045, exclusive of a translation termination codon.

11. The non-naturally occurring recombinant DNA molecule of claim 10 further comprising a translation termination codon, wherein said translation termination codon is TGA, TAA or TAG and it is immediately downstream of nucleotide 1045.

12. The non-naturally occurring recombinant DNA molecule of claim 1 encoding an amino acid sequence as given in SEQ ID NO:6, amino acids 1 to 307.

13. The non-naturally occurring recombinant DNA molecule of claim 12 wherein the nucleotide sequence encoding said calcium-dependent lectin polypeptide is as given in SEQ ID NO:5, nucleotides 88 to 1008, exclusive of a translation termination codon.

14. The non-naturally occurring recombinant DNA molecule of claim 12 further comprising a second region encoding a signal sequence as given in SEQ ID NO:6, amino acids −18 to −1 immediately upstream of the first region encoding the amino acid sequence of SEQ ID NO:6, amino acids 1 to 307.

15. The non-naturally occurring recombinant DNA molecule of claim 12 wherein said second and said first regions together have a nucleotide sequence as given in SEQ ID NO:5, nucleotides 34 to 1008, exclusive of a translation termination codon.

16. The non-naturally occurring recombinant DNA molecule of claim 15 further comprising a translation termination codon, wherein said translation termination codon is TGA, TAA or TAG and it is immediately downstream of nucleotide 1008.

17. A host cell transformed or transfected to contain the recombinant DNA molecule of claim 1.

18. The host cell of claim 17, wherein the recombinant DNA molecule comprises a first region encoding an amino acid sequence as given in SEQ ID NO:2, amino acids 1 to 295.

19. The host cell of claim 17, wherein the recombinant DNA molecule encodes an amino acid sequence as given in SEQ ID NO:4, amino acids 1 to 297.

20. The host cell of claim 17, wherein the recombinant DNA molecule encoding an amino acid sequence as given in SEQ ID NO:6, amino acids 1 to 307.

21. A method for recombinantly producing a mature calcium-dependent lectin polypeptide in a host cell, said method comprising the steps of:

a) infecting or transforming a host cell capable of expressing a mature calcium-dependent lectin coding sequence with a vector comprising a promoter active in said host cell operably linked to a coding region for said mature lectin polypeptide having an amino acid sequence as set forth in SEQ ID NO:2, amino acids 1 to 295; SEQ ID NO:4, amino acids 1 to 297; or SEQ ID NO:6, amino acids 1 to 307, to produce a recombinant host cell; and b) culturing the recombinant host cell under conditions wherein said calcium-dependent lectin polypeptide is expressed.

22. A nucleic acid molecule useful for the identification of calcium-dependent lectin polypeptide coding sequences, said nucleic acid molecule comprising a nucleotide sequence as given in SEQ ID NO:1, nucleotides 118–518, SEQ ID NO:3, nucleotides 305–554 or SEQ ID NO:5, nucleotides 268–517, or a nucleotide sequence complementary to one of the foregoing.

23. A mature calcium-dependent lectin polypeptide coding sequence which is hybridizable under conditions of moderate stringency to a nucleic acid molecule encoding a mature lectin polypeptide having an amino acid sequence as set forth in SEQ ID NO:2, amino acids 1 to 295; an amino acid sequence as set forth in SEQ ID NO:4, amino acids 1 to 297; or an amino acid sequence as set forth in SEQ ID NO:6, amino acids 1 to 307, wherein said conditions of moderate stringency are hybridization and/or washing at 50 to 65° C., 1×SSC, and 0.1% SDS.

* * * * *

UNITED STATES PATENT AND TRADEMARK OFFICE
CERTIFICATE OF CORRECTION

PATENT NO.    : 6,146,849                                          Page 1 of 1
DATED         : November 14, 2000
INVENTOR(S)   : Pierce et al.

It is certified that error appears in the above-identified patent and that said Letters Patent is hereby corrected as shown below:

Columns 29 and 30,
Table 1, second line of the heading, please replace "See also SEQ ID NO:2 and SEQ ID NO:3." with -- See also SEQ ID NO:1 and SEQ ID NO:2. --.

Columns 31 and 32,
Table 1, second line of the heading, please replace "See also SEQ ID NO:2 and SEQ ID NO:3." with -- See also SEQ ID NO:1 and SEQ ID NO:2. --.

Columns 33 and 34,
Table 3, after the heading, please insert -- See also SEQ ID NO:3 and SEQ ID NO:4. --.
Table 4, after the heading, please insert -- See also SEQ ID NO:5 and SEQ ID NO:6. --.

Column 63,
Line 32, please replace "claim 2" with -- claim 4 --.

Signed and Sealed this

Fourth Day of February, 2003

JAMES E. ROGAN
*Director of the United States Patent and Trademark Office*

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 1090 base pairs
      (B) TYPE: nucleic acid
      (C) STRANDEDNESS: double
      (D) TOPOLOGY: Not Relevant (ii) MOLECULE TYPE: cDNA to mRNA (iii) HYPOTHETICAL: NO (ix) FEATURE:
      (A) NAME/KEY: CDS
      (B) LOCATION: 33..974

(ix) FEATURE:
      (A) NAME/KEY: sig_peptide
      (B) LOCATION: 33..86

(ix) FEATURE:
      (A) NAME/KEY: mat_peptide
      (B) LOCATION: 87..971

(xi) SEQUENCE DESCRIPTION: SEQ ID NO:1:

```
GGCTTGGAAC TTGGTACTAA GCTCCATGAA AG ATG CTG GTG CAC ATT CTT CTC         53
                                    Met Leu Val His Ile Leu Leu
                                    -18             -15

CTG CTG GTG ACT GGT GGG CTC TCT CAG TCT TGT GAC CCT GTT GTA ATA         101
Leu Leu Val Thr Gly Gly Leu Ser Gln Ser Cys Asp Pro Val Val Ile
    -10              -5                  1                   5

GTA GCC TCA AAA AAC ATG GTG AAG CAG CTG GAT TGT GAT AAA TTC AGA         149
Val Ala Ser Lys Asn Met Val Lys Gln Leu Asp Cys Asp Lys Phe Arg
                 10                  15                  20

AAC TGC AAG GAG ATC AAA GAT TCA AAC GAA GAA GCA CAA GAT GGA ATA         197
Asn Cys Lys Glu Ile Lys Asp Ser Asn Glu Glu Ala Gln Asp Gly Ile
             25                  30                  35

TAC ACA CTG ACC TCT CCA GAT GGG ATA TCC TAC CAG ACC TTC TGT GAC         245
Tyr Thr Leu Thr Ser Pro Asp Gly Ile Ser Tyr Gln Thr Phe Cys Asp
         40                  45                  50

ATG ACT ACA AAT GGA GGA GGA TGG ACT TTG GTG GCG AGT GTT CAT GAG         293
Met Thr Thr Asn Gly Gly Gly Trp Thr Leu Val Ala Ser Val His Glu
     55                  60                  65

AAC AAC ATG GCA GGG AAG TGC ACT ATA GGG GAT CGC TGG TCC AGC CAA         341
Asn Asn Met Ala Gly Lys Cys Thr Ile Gly Asp Arg Trp Ser Ser Gln
 70                  75                  80                  85

CAG GGG AAT CGA GCT GAC TAT CCA GAG GGC GAT GGC AAC TGG GCA AAC         389
Gln Gly Asn Arg Ala Asp Tyr Pro Glu Gly Asp Gly Asn Trp Ala Asn
                 90                  95                 100

TAT AAT ACA TTT GGA TCA GCT GGT GGC GCA ACT AGT GAT GAC TAC AAG         437
Tyr Asn Thr Phe Gly Ser Ala Gly Gly Ala Thr Ser Asp Asp Tyr Lys
             105                 110                 115

AAT CCT GGC TAT TAT GAT ATT GAA GCA TAT AAC CTT GGG GTG TGG CAC         485
Asn Pro Gly Tyr Tyr Asp Ile Glu Ala Tyr Asn Leu Gly Val Trp His
         120                 125                 130

GTG CCC AAC AAG ACT CCC CTG AGT GTT TGG AGG AAT TCA TCG CTA CAG         533
Val Pro Asn Lys Thr Pro Leu Ser Val Trp Arg Asn Ser Ser Leu Gln
     135                 140                 145

AGA TAC CGT ACA ACA GAT GGC ATC CTT TTC AAA CAT GGA GGA AAC CTC         581
```

-continued

```
Arg Tyr Arg Thr Thr Asp Gly Ile Leu Phe Lys His Gly Gly Asn Leu
150                 155                 160                 165

TTC AGT CTG TAT CGG ATC TAT CCA GTG AAA TAT GGT ATA GGA AGC TGC          629
Phe Ser Leu Tyr Arg Ile Tyr Pro Val Lys Tyr Gly Ile Gly Ser Cys
            170                 175                 180

TCA AAG GAC AGT GGC CCA ACT GTG CCA GTA GTG TAC GAT CTT GGA AGT          677
Ser Lys Asp Ser Gly Pro Thr Val Pro Val Val Tyr Asp Leu Gly Ser
                185                 190                 195

GCT AAT TTA ACA GCT TCT TTC TAC TCT CCA GGT TTC AGA AGT CAG TTT          725
Ala Asn Leu Thr Ala Ser Phe Tyr Ser Pro Gly Phe Arg Ser Gln Phe
            200                 205                 210

ACC CCT GGC TAT ATC CAA TTT CGG CCA ATT AAC ACT GAA AAA GCT GCT          773
Thr Pro Gly Tyr Ile Gln Phe Arg Pro Ile Asn Thr Glu Lys Ala Ala
        215                 220                 225

CTG GCG CTA TGT CCG GGA ATG AAG ATG GAG TCA TGC AAT GTG GAA CAT          821
Leu Ala Leu Cys Pro Gly Met Lys Met Glu Ser Cys Asn Val Glu His
230                 235                 240                 245

GTG TGC ATA GGA GGA GGT GGC TAC TTT CCA GAA GCA GAC CCT CGG CAA          869
Val Cys Ile Gly Gly Gly Gly Tyr Phe Pro Glu Ala Asp Pro Arg Gln
                250                 255                 260

TGT GGA GAC TTT GCA GCC TAT GAC TTT AAT GGA TAT GGA ACC AAA AAG          917
Cys Gly Asp Phe Ala Ala Tyr Asp Phe Asn Gly Tyr Gly Thr Lys Lys
            265                 270                 275

TTT AAC AGT GCG GGC ATA GAG ATA ACT GAG GCC GCT GTA TTA CTT TTC          965
Phe Asn Ser Ala Gly Ile Glu Ile Thr Glu Ala Ala Val Leu Leu Phe
        280                 285                 290

TAT CTA TGA TCTGAAATCT TACTAAAAAT AACTAGTACA AAAACAAGAA                 1014
Tyr Leu  *
295

TAGTAAGTGC ATTGTTTGGC AACTTTATTA AACCACAATC CTGTCTTGAG ATAAGCCGAA        1074

TTCCAGCACA CTGGCG                                                        1090
```

(2) INFORMATION FOR SEQ ID NO:2:

(i) SEQUENCE CHARACTERISTICS:
        (A) LENGTH: 313 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Val His Ile Leu Leu Leu Val Thr Gly Gly Leu Ser Gln
-18             -15                 -10                 -5

Ser Cys Asp Pro Val Val Ile Val Ala Ser Lys Asn Met Val Lys Gln
            1               5                   10

Leu Asp Cys Asp Lys Phe Arg Asn Cys Lys Glu Ile Lys Asp Ser Asn
15                  20                  25                  30

Glu Glu Ala Gln Asp Gly Ile Tyr Thr Leu Thr Ser Pro Asp Gly Ile
                35                  40                  45

Ser Tyr Gln Thr Phe Cys Asp Met Thr Thr Asn Gly Gly Gly Trp Thr
            50                  55                  60

Leu Val Ala Ser Val His Glu Asn Asn Met Ala Gly Lys Cys Thr Ile
        65                  70                  75

Gly Asp Arg Trp Ser Ser Gln Gln Gly Asn Arg Ala Asp Tyr Pro Glu
    80                  85                  90

Gly Asp Gly Asn Trp Ala Asn Tyr Asn Thr Phe Gly Ser Ala Gly Gly
95                  100                 105                 110
```

```
Ala Thr Ser Asp Asp Tyr Lys Asn Pro Gly Tyr Tyr Asp Ile Glu Ala
            115                 120                 125

Tyr Asn Leu Gly Val Trp His Val Pro Asn Lys Thr Pro Leu Ser Val
        130                 135                 140

Trp Arg Asn Ser Ser Leu Gln Arg Tyr Arg Thr Thr Asp Gly Ile Leu
    145                 150                 155

Phe Lys His Gly Gly Asn Leu Phe Ser Leu Tyr Arg Ile Tyr Pro Val
160                 165                 170

Lys Tyr Gly Ile Gly Ser Cys Ser Lys Asp Ser Gly Pro Thr Val Pro
175                 180                 185                 190

Val Val Tyr Asp Leu Gly Ser Ala Asn Leu Thr Ala Ser Phe Tyr Ser
            195                 200                 205

Pro Gly Phe Arg Ser Gln Phe Thr Pro Gly Tyr Ile Gln Phe Arg Pro
        210                 215                 220

Ile Asn Thr Glu Lys Ala Ala Leu Ala Leu Cys Pro Gly Met Lys Met
    225                 230                 235

Glu Ser Cys Asn Val Glu His Val Cys Ile Gly Gly Gly Tyr Phe
240                 245                 250

Pro Glu Ala Asp Pro Arg Gln Cys Gly Asp Phe Ala Ala Tyr Asp Phe
255                 260                 265                 270

Asn Gly Tyr Gly Thr Lys Lys Phe Asn Ser Ala Gly Ile Glu Ile Thr
            275                 280                 285

Glu Ala Ala Val Leu Leu Phe Tyr Leu
            290                 295

(2) INFORMATION FOR SEQ ID NO:3:

(i) SEQUENCE CHARACTERISTICS:
        (A) LENGTH: 1144 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (ix) FEATURE:
        (A) NAME/KEY: CDS
        (B) LOCATION: 107..1048

(ix) FEATURE:
        (A) NAME/KEY: sig_peptide
        (B) LOCATION: 107..154

(ix) FEATURE:
        (A) NAME/KEY: mat_peptide
        (B) LOCATION: 155..1045

(xi) SEQUENCE DESCRIPTION: SEQ ID NO:3:

TTGGAGAAAG CTGCACTCTG TTGAGCTCCA GGGCGCAGTG GAGGGAGGGA GTGAAGGAGC      60

TCTCTGTACC CAAGGAAAGT GCAGCTGAGA CTCAGACAAG ATTACA ATG AAC CAA        115
                                                   Met Asn Gln
                                                   -16 -15

CTC AGC TTC CTG CTG TTT CTC ATA GCG ACC ACC AGA GGA TGG AGT ACA       163
Leu Ser Phe Leu Leu Phe Leu Ile Ala Thr Thr Arg Gly Trp Ser Thr
        -10                 -5                  1

GAT GAG GCT AAT ACT TAC TTC AAG GAA TGG ACC TGT TCT TCG TCT CCA       211
Asp Glu Ala Asn Thr Tyr Phe Lys Glu Trp Thr Cys Ser Ser Ser Pro
        5                   10                  15

TCT CTG CCC AGA AGC TGC AAG GAA ATC AAA GAC GAA TGT CCT AGT GCA       259
Ser Leu Pro Arg Ser Cys Lys Glu Ile Lys Asp Glu Cys Pro Ser Ala
```

```
       20                  25                  30                  35
TTT GAT GGC CTG TAT TTT CTC CGC ACT GAG AAT GGT GTT ATC TAC CAG         307
Phe Asp Gly Leu Tyr Phe Leu Arg Thr Glu Asn Gly Val Ile Tyr Gln
                40                  45                  50

ACC TTC TGT GAC ATG ACC TCT GGG GGT GGC GGC TGG ACC CTG GTG GCC         355
Thr Phe Cys Asp Met Thr Ser Gly Gly Gly Gly Trp Thr Leu Val Ala
                    55                  60                  65

AGC GTG CAT GAG AAT GAC ATG CGT GGG AAG TGC ACG GTG GGC GAT CGC         403
Ser Val His Glu Asn Asp Met Arg Gly Lys Cys Thr Val Gly Asp Arg
                70                  75                  80

TGG TCC AGT CAG CAG GGC AGC AAA GCA GAC TAC CCA GAG GGG GAC GGC         451
Trp Ser Ser Gln Gln Gly Ser Lys Ala Asp Tyr Pro Glu Gly Asp Gly
            85                  90                  95

AAC TGG GCC AAC TAC AAC ACC TTT GGA TCT GCA GAG GCG GGC ACG AGC         499
Asn Trp Ala Asn Tyr Asn Thr Phe Gly Ser Ala Glu Ala Gly Thr Ser
100                 105                 110                 115

GAT GAC TAC AAG AAC CCT GGC TAC TAC GAC ATC CAG GCC AAG GAC CTG         547
Asp Asp Tyr Lys Asn Pro Gly Tyr Tyr Asp Ile Gln Ala Lys Asp Leu
                    120                 125                 130

GGC ATC TGG CAC GTG CCC AAT AAG TCC CCC ATG CAG CAC TGG AGA AAC         595
Gly Ile Trp His Val Pro Asn Lys Ser Pro Met Gln His Trp Arg Asn
                135                 140                 145

AGC TCC CTG CTG AGG TAC CGC ACG GAC ACT GGC TTC CTC CAG ACA CTG         643
Ser Ser Leu Leu Arg Tyr Arg Thr Asp Thr Gly Phe Leu Gln Thr Leu
            150                 155                 160

GGA CAT AAT CTG TTT GGC ATC TAC CAG AAA TAT CCA GTG AAA TAT GGA         691
Gly His Asn Leu Phe Gly Ile Tyr Gln Lys Tyr Pro Val Lys Tyr Gly
        165                 170                 175

GAA GGA AAG TGT TGG ACT GAC AAC GGC CCG GTG ATC CCT GTG GTC TAT         739
Glu Gly Lys Cys Trp Thr Asp Asn Gly Pro Val Ile Pro Val Val Tyr
180                 185                 190                 195

GAT TTT GGC GAC GCC CAG AAA ACA GCA TCT TAT TAC TCA CCC TAT GGC         787
Asp Phe Gly Asp Ala Gln Lys Thr Ala Ser Tyr Tyr Ser Pro Tyr Gly
                    200                 205                 210

CAG CGG GAA TTC ACT GCG GGA TTT GTT CAG TTC AGG GTA TTT AAT AAC         835
Gln Arg Glu Phe Thr Ala Gly Phe Val Gln Phe Arg Val Phe Asn Asn
                215                 220                 225

GAG AGA GCA GCC AAC GCC TTG TGT GCT GGA ATG AGG GTC ACC GGA TGT         883
Glu Arg Ala Ala Asn Ala Leu Cys Ala Gly Met Arg Val Thr Gly Cys
            230                 235                 240

AAC ACT GAG CAC CAC TGC ATT GGT GGA GGA GGA TAC TTT CCA GAG GCC         931
Asn Thr Glu His His Cys Ile Gly Gly Gly Gly Tyr Phe Pro Glu Ala
        245                 250                 255

AGT CCC CAG CAG TGT GGA GAT TTT TCT GGT TTT GAT TGG AGT GGA TAT         979
Ser Pro Gln Gln Cys Gly Asp Phe Ser Gly Phe Asp Trp Ser Gly Tyr
260                 265                 270                 275

GGA ACT CAT GTT GGT TAC AGC AGC AGC CGT GAG ATA ACT GAG GCA GCT        1027
Gly Thr His Val Gly Tyr Ser Ser Ser Arg Glu Ile Thr Glu Ala Ala
                    280                 285                 290

GTG CTT CTA TTC TAT CGT TGA GAGTTTTGTG GGAGGGAACC CAGACCTCTC           1078
Val Leu Leu Phe Tyr Arg *
                295

CTCCCAACCA TGAGATCCCA AGGATGGAGA ACAACTTACC CAGTAGCTAG AATGTTAATG      1138

GCGGCG                                                                 1144

(2) INFORMATION FOR SEQ ID NO:4:

(i) SEQUENCE CHARACTERISTICS:
        (A) LENGTH: 313 amino acids
```

(B) TYPE: amino acid
            (D) TOPOLOGY: linear (ii) MOLECULE TYPE: protein (xi) SEQUENCE DESCRIPTION: SEQ ID NO:4:

Met Asn Gln Leu Ser Phe Leu Leu Phe Leu Ile Ala Thr Thr Arg Gly
-16 -15              -10                  -5

Trp Ser Thr Asp Glu Ala Asn Thr Tyr Phe Lys Glu Trp Thr Cys Ser
 1           5                   10                  15

Ser Ser Pro Ser Leu Pro Arg Ser Cys Lys Glu Ile Lys Asp Glu Cys
            20                  25                  30

Pro Ser Ala Phe Asp Gly Leu Tyr Phe Leu Arg Thr Glu Asn Gly Val
            35                  40                  45

Ile Tyr Gln Thr Phe Cys Asp Met Thr Ser Gly Gly Gly Gly Trp Thr
 50                  55                  60

Leu Val Ala Ser Val His Glu Asn Asp Met Arg Gly Lys Cys Thr Val
 65                  70                  75                  80

Gly Asp Arg Trp Ser Ser Gln Gln Gly Ser Lys Ala Asp Tyr Pro Glu
            85                  90                  95

Gly Asp Gly Asn Trp Ala Asn Tyr Asn Thr Phe Gly Ser Ala Glu Ala
            100                 105                 110

Gly Thr Ser Asp Asp Tyr Lys Asn Pro Gly Tyr Tyr Asp Ile Gln Ala
            115                 120                 125

Lys Asp Leu Gly Ile Trp His Val Pro Asn Lys Ser Pro Met Gln His
130                 135                 140

Trp Arg Asn Ser Ser Leu Leu Arg Tyr Arg Thr Asp Thr Gly Phe Leu
145                 150                 155                 160

Gln Thr Leu Gly His Asn Leu Phe Gly Ile Tyr Gln Lys Tyr Pro Val
            165                 170                 175

Lys Tyr Gly Glu Gly Lys Cys Trp Thr Asp Asn Gly Pro Val Ile Pro
            180                 185                 190

Val Val Tyr Asp Phe Gly Asp Ala Gln Lys Thr Ala Ser Tyr Tyr Ser
            195                 200                 205

Pro Tyr Gly Gln Arg Glu Phe Thr Ala Gly Phe Val Gln Phe Arg Val
210                 215                 220

Phe Asn Asn Glu Arg Ala Ala Asn Ala Leu Cys Ala Gly Met Arg Val
225                 230                 235                 240

Thr Gly Cys Asn Thr Glu His His Cys Ile Gly Gly Gly Gly Tyr Phe
            245                 250                 255

Pro Glu Ala Ser Pro Gln Gln Cys Gly Asp Phe Ser Gly Phe Asp Trp
            260                 265                 270

Ser Gly Tyr Gly Thr His Val Gly Tyr Ser Ser Ser Arg Glu Ile Thr
            275                 280                 285

Glu Ala Ala Val Leu Leu Phe Tyr Arg
290                 295

(2) INFORMATION FOR SEQ ID NO:5:

(i) SEQUENCE CHARACTERISTICS:
        (A) LENGTH: 1139 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (ix) FEATURE:
        (A) NAME/KEY: CDS
        (B) LOCATION: 34..1011

(ix) FEATURE:
        (A) NAME/KEY: sig_peptide
        (B) LOCATION: 34..87

(ix) FEATURE:
        (A) NAME/KEY: mat_peptide
        (B) LOCATION: 88..1008

(xi) SEQUENCE DESCRIPTION: SEQ ID NO:5:

```
CGGGGGAACT ATCAGCTCCT GGCATCTGTA AGG ATG CTG TCC ATG CTG AGG ACA          54
                                    Met Leu Ser Met Leu Arg Thr
                                    -18             -15

ATG ACC AGA CTC TGC TTC CTG TTA TTC TTC TCT GTG GCC ACC AGT GGG          102
Met Thr Arg Leu Cys Phe Leu Leu Phe Phe Ser Val Ala Thr Ser Gly
        -10              -5                   1               5

TGC AGT GCA GCA GCA GCC TCT TCT CTT GAG ATG CTC TCG AGG GAA TTC          150
Cys Ser Ala Ala Ala Ala Ser Ser Leu Glu Met Leu Ser Arg Glu Phe
                10              15                  20

GAA ACC TGT GCC TTC TCC TTT TCT TCC CTG CCT AGA AGC TGC AAA GAA          198
Glu Thr Cys Ala Phe Ser Phe Ser Ser Leu Pro Arg Ser Cys Lys Glu
            25                  30                  35

ATC AAG GAA CGC TGC CAT AGT GCA GGT GAT GGC CTG TAT TTT CTC CGC          246
Ile Lys Glu Arg Cys His Ser Ala Gly Asp Gly Leu Tyr Phe Leu Arg
        40                  45                  50

ACC AAG AAT GGT GTT GTC TAC CAG ACC TTC TGT GAC ATG ACT TCT GGG          294
Thr Lys Asn Gly Val Val Tyr Gln Thr Phe Cys Asp Met Thr Ser Gly
    55                  60                  65

GGT GGC GGC TGG ACC CTG GTG GCC AGC GTG CAC GAG AAT GAC ATG CGT          342
Gly Gly Gly Trp Thr Leu Val Ala Ser Val His Glu Asn Asp Met Arg
70                  75                  80                  85

GGG AAG TGC ACG GTG GGT GAT CGC TGG TCC AGT CAG CAG GGC AAC AAA          390
Gly Lys Cys Thr Val Gly Asp Arg Trp Ser Ser Gln Gln Gly Asn Lys
                90                  95                  100

GCA GAC TAC CCA GAG GGG GAT GGC AAC TGG GCC AAC TAC AAC ACC TTT          438
Ala Asp Tyr Pro Glu Gly Asp Gly Asn Trp Ala Asn Tyr Asn Thr Phe
            105                 110                 115

GGA TCT GCA GAG GCG GCC ACG AGC GAT GAC TAC AAG AAC CCT GGC TAC          486
Gly Ser Ala Glu Ala Ala Thr Ser Asp Asp Tyr Lys Asn Pro Gly Tyr
        120                 125                 130

TAC GAC ATC CAG GCC AAG GAC CTG GGC ATC TGG CAT GTG CCC AAC AAG          534
Tyr Asp Ile Gln Ala Lys Asp Leu Gly Ile Trp His Val Pro Asn Lys
    135                 140                 145

TCC CCC ATG CAG CAT TGG AGA AAC AGC GCC CTG CTG AGG TAC CGC ACC          582
Ser Pro Met Gln His Trp Arg Asn Ser Ala Leu Leu Arg Tyr Arg Thr
150                 155                 160                 165

AAC ACT GGC TTC CTC CAG AGA CTG GGA CAT AAT CTG TTT GGC ATC TAC          630
Asn Thr Gly Phe Leu Gln Arg Leu Gly His Asn Leu Phe Gly Ile Tyr
                170                 175                 180

CAG AAA TAC CCA GTG AAA TAC AGA TCA GGG AAA TGT TGG AAT GAC AAT          678
Gln Lys Tyr Pro Val Lys Tyr Arg Ser Gly Lys Cys Trp Asn Asp Asn
            185                 190                 195

GGC CCA GCC ATA CCT GTG GTC TAT GAC TTT GGT GAT GCT AAG AAG ACT          726
Gly Pro Ala Ile Pro Val Val Tyr Asp Phe Gly Asp Ala Lys Lys Thr
        200                 205                 210

GCA TCT TAT TAC TCA CCG TAT GGT CAA CGG GAA TTT GTT GCA GGA TTC          774
Ala Ser Tyr Tyr Ser Pro Tyr Gly Gln Arg Glu Phe Val Ala Gly Phe
    215                 220                 225
```

```
GTT CAG TTC CGG GTG TTT AAT AAC GAG AGA GCA GCC AAC GCC CTT TGT        822
Val Gln Phe Arg Val Phe Asn Asn Glu Arg Ala Ala Asn Ala Leu Cys
230                 235                 240                 245

GCT GGG ATA AAA GTT ACT GGC TGT AAC ACT GAG CAT CAC TGC ATC GGT        870
Ala Gly Ile Lys Val Thr Gly Cys Asn Thr Glu His His Cys Ile Gly
                250                 255                 260

GGA GGA GGG TTC TTC CCA CAG GGC AAA CCC CGT CAG TGT GGG GAC TTC        918
Gly Gly Gly Phe Phe Pro Gln Gly Lys Pro Arg Gln Cys Gly Asp Phe
            265                 270                 275

TCC GCC TTT GAC TGG GAT GGA TAT GGA ACT CAC GTT AAG AGC ACC TCC        966
Ser Ala Phe Asp Trp Asp Gly Tyr Gly Thr His Val Lys Ser Thr Ser
        280                 285                 290

AGT CGG GAG ATA ACG GAG GCG CCT GTA CTC TTG TTC TAT AGA TGA           1011
Ser Arg Glu Ile Thr Glu Ala Pro Val Leu Leu Phe Tyr Arg *
    295                 300                 305

GACAGAGCTC TCCGGTGTCA GGGCGAGAAC CCATCTTCCA ACCCCGGCTA TTTGGAGACG     1071

GAAAAACTGG AATTCTAACA AGGAGGAGAG GAGACTAAAT CACATCAATT TGCCCAAAAA     1131

AAAAACCG                                                              1139
```

(2) INFORMATION FOR SEQ ID NO:6:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Ser Met Leu Arg Thr Met Thr Arg Leu Cys Phe Leu Leu Phe
-18             -15                 -10                 -5

Phe Ser Val Ala Thr Ser Gly Cys Ser Ala Ala Ala Ser Ser Leu
            1               5                   10

Glu Met Leu Ser Arg Glu Phe Glu Thr Cys Ala Phe Ser Phe Ser Ser
15              20                  25                  30

Leu Pro Arg Ser Cys Lys Glu Ile Lys Glu Arg Cys His Ser Ala Gly
                35                  40                  45

Asp Gly Leu Tyr Phe Leu Arg Thr Lys Asn Gly Val Val Tyr Gln Thr
            50                  55                  60

Phe Cys Asp Met Thr Ser Gly Gly Gly Gly Trp Thr Leu Val Ala Ser
        65                  70                  75

Val His Glu Asn Asp Met Arg Gly Lys Cys Thr Val Gly Asp Arg Trp
    80                  85                  90

Ser Ser Gln Gln Gly Asn Lys Ala Asp Tyr Pro Glu Gly Asp Gly Asn
95                  100                 105                 110

Trp Ala Asn Tyr Asn Thr Phe Gly Ser Ala Glu Ala Ala Thr Ser Asp
            115                 120                 125

Asp Tyr Lys Asn Pro Gly Tyr Tyr Asp Ile Gln Ala Lys Asp Leu Gly
            130                 135                 140

Ile Trp His Val Pro Asn Lys Ser Pro Met Gln His Trp Arg Asn Ser
        145                 150                 155

Ala Leu Leu Arg Tyr Arg Thr Asn Thr Gly Phe Leu Gln Arg Leu Gly
    160                 165                 170

His Asn Leu Phe Gly Ile Tyr Gln Lys Tyr Pro Val Lys Tyr Arg Ser
175                 180                 185                 190

Gly Lys Cys Trp Asn Asp Asn Gly Pro Ala Ile Pro Val Val Tyr Asp
            195                 200                 205
```

```
Phe Gly Asp Ala Lys Lys Thr Ala Ser Tyr Tyr Ser Pro Tyr Gly Gln
            210                 215                 220

Arg Glu Phe Val Ala Gly Phe Val Gln Phe Arg Val Phe Asn Asn Glu
            225                 230                 235

Arg Ala Ala Asn Ala Leu Cys Ala Gly Ile Lys Val Thr Gly Cys Asn
            240                 245                 250

Thr Glu His His Cys Ile Gly Gly Gly Phe Phe Pro Gln Gly Lys
255                 260                 265                 270

Pro Arg Gln Cys Gly Asp Phe Ser Ala Phe Asp Trp Asp Gly Tyr Gly
            275                 280                 285

Thr His Val Lys Ser Thr Ser Ser Arg Glu Ile Thr Glu Ala Pro Val
            290                 295                 300

Leu Leu Phe Tyr Arg
        305

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:7:

Glu Ser Cys Asn Ala Glu His Val Cys Ile Gly Gly Gly Tyr Phe
1               5                   10                  15

Pro Glu Ala Asp Pro Arg
            20

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:8:

Ser Gln Phe Asp Thr Pro Gly Tyr Ile Gln Phe Arg Pro Ile Asn Thr
1               5                   10                  15

Glu Lys (2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Degenerate
            oligonucleotide."

(iii) HYPOTHETICAL: NO (xi) SEQUENCE DESCRIPTION: SEQ ID NO:9:
```

```
CARTTYACCC GGTAYATHCA RTT                                              23

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Degenerate
             oligonucleotide."

(iii) HYPOTHETICAL: NO (xi) SEQUENCE DESCRIPTION: SEQ ID NO:10:

CCCDATRCAA CRTGYTCGCR TTRCA                                            25

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO (iv) ANTI-SENSE: NO (xi) SEQUENCE DESCRIPTION: SEQ ID NO:11:

GGAACTTGGT ACTAAGCTCC ATGAAAG                                          27

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO (xi) SEQUENCE DESCRIPTION: SEQ ID NO:12:

ATCTCAAGAC AGGATTGTGG TTTAATAAAG                                       30

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO (iv) ANTI-SENSE: NO (xi) SEQUENCE DESCRIPTION: SEQ ID NO:13:

CCCGTCGACG AACCTGTTGT AATAGTAGCC TCAAAA                                36
```

-continued (2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:14:

CCCCTGCAGT CATAGATAGA AAAGTAATAC AGCGGCCTC                              39

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:15:

CAGACCTTCT GTGACATGAC CTCT                                            24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:16:

AAGATGCCCA GGTCCTTGGC CTGG                                            24

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:17:

CCCGTCGACT GGAGTACAGA TGAGGCTAAT ACTTAC                              36

(2) INFORMATION FOR SEQ ID NO:18:

(i) SEQUENCE CHARACTERISTICS:

(A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:18:

CCCAAGCTTT CAACGATAGA ATAGAAGCAC AGCTGC                                  36

(2) INFORMATION FOR SEQ ID NO:19:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (iv) ANTI-SENSE: NO (xi) SEQUENCE DESCRIPTION: SEQ ID NO:19:

CCCGTCGACT CTTCTCTTGA GATGCTCTCG AGGGAA                                  36

(2) INFORMATION FOR SEQ ID NO:20:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:20:

CCCAAGCTTT CATCTATAGA ACAAGAGTAC AGGCGC                                  36

(2) INFORMATION FOR SEQ ID NO:21:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (iv) ANTI-SENSE: NO (xi) SEQUENCE DESCRIPTION: SEQ ID NO:21:

ATACTTTCCA GAGGCCAGTC CCCAG                                              25

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:22:

AGGTCTGGGT TCCCTCCCAC AAAAC                                        25

(2) INFORMATION FOR SEQ ID NO:23:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (iv) ANTI-SENSE: NO (xi) SEQUENCE DESCRIPTION: SEQ ID NO:23:

GTTCTTCCCA CAGGGCAAAC CCCGT                                        25

(2) INFORMATION FOR SEQ ID NO:24:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:24:

TCTGCCCTGA CACCGGAGAG CTCTG                                        25

(2) INFORMATION FOR SEQ ID NO:25:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (iv) ANTI-SENSE: NO (xi) SEQUENCE DESCRIPTION: SEQ ID NO:25:

GGGCCCTGAA AGATGCTGGT GCACATTCTT CTCCTG                            36

(2) INFORMATION FOR SEQ ID NO:26:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid (A) DESCRIPTION: /desc = "Oligonucleotide."

(iii) HYPOTHETICAL: NO (xi) SEQUENCE DESCRIPTION: SEQ ID NO:26:

CCCCTGCAGT CATAGATAGA AAAGTAATAC AGCGGCCTC                                    39

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:27:

GGGCCCGACT CAGACAAGAT TACAATGAAC CAACTC                                       36

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:28:

ACTAGTAGGT CTGGGTTCCC TCCCACAAAA CTCTCA                                       36

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:29:

GGGCCCTCTG TAAGGATGCT GTCCATGCTG AGGACA                                       36

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO

-continued (xi) SEQUENCE DESCRIPTION: SEQ ID NO:30:

ACTAGTCTCG CCCTGACACC GGAGAGCTCT GTCTCA        36